(12) United States Patent
Pazolli et al.

(10) Patent No.: US 11,998,544 B2
(45) Date of Patent: Jun. 4, 2024

(54) METHODS OF USING SPLICING MODULATORS

(71) Applicant: EISAI R&D MANAGEMENT CO., LTD., Tokyo (JP)

(72) Inventors: Ermira Pazolli, Wayland, MA (US); Silvia Buonamici, Boston, MA (US); James Palacino, Wellesley, MA (US); Michael Seiler, Belmont, MA (US); Ping Zhu, Acton, MA (US); Evan Barry, Milford, MA (US); Lihua Yu, Acton, MA (US)

(73) Assignee: EISAI R&D MANAGEMENT CO., LTD., Tokyo (JP)

(*) Notice: Subject to any disclaimer, the term of this patent is extended or adjusted under 35 U.S.C. 154(b) by 431 days.

(21) Appl. No.: 17/059,876

(22) PCT Filed: May 31, 2019

(86) PCT No.: PCT/US2019/034992
§ 371 (c)(1),
(2) Date: Nov. 30, 2020

(87) PCT Pub. No.: WO2019/232433
PCT Pub. Date: Dec. 5, 2019

(65) Prior Publication Data
US 2021/0346371 A1 Nov. 11, 2021

Related U.S. Application Data

(60) Provisional application No. 62/679,699, filed on Jun. 1, 2018, provisional application No. 62/679,696, filed on Jun. 1, 2018.

(51) Int. Cl.
| | | |
|---|---|---|
| A61K 31/496 | (2006.01) | |
| A61K 35/17 | (2015.01) | |
| A61K 38/19 | (2006.01) | |
| A61K 38/20 | (2006.01) | |
| A61K 38/21 | (2006.01) | |
| A61K 39/00 | (2006.01) | |
| A61K 39/39 | (2006.01) | |
| A61K 39/395 | (2006.01) | |
| A61K 47/68 | (2017.01) | |

(52) U.S. Cl.
CPC ............ *A61K 31/496* (2013.01); *A61K 35/17* (2013.01); *A61K 38/191* (2013.01); *A61K 38/2013* (2013.01); *A61K 38/2066* (2013.01); *A61K 38/208* (2013.01); *A61K 38/2086* (2013.01); *A61K 38/217* (2013.01); *A61K 39/0011* (2013.01); *A61K 39/39* (2013.01); *A61K 39/3955* (2013.01); *A61K 47/6803* (2017.08); *A61K 2039/6031* (2013.01); *A61K 2039/6037* (2013.01); *A61K 2039/6056* (2013.01); *A61K 2039/6081* (2013.01)

(58) Field of Classification Search
CPC ....................... A61K 31/496; A61K 47/6803
See application file for complete search history.

(56) References Cited

U.S. PATENT DOCUMENTS

| | | | | |
|---|---|---|---|---|
| 5,595,756 | A | * | 1/1997 | Bally .................. A61K 9/1272 264/4.1 |
| 7,667,052 | B2 | | 2/2010 | Mizui et al. |
| 7,816,401 | B2 | | 10/2010 | Kanada et al. |
| 10,322,192 | B2 | | 6/2019 | Albone et al. |
| 10,548,986 | B2 | | 2/2020 | Albone et al. |
| 2015/0202291 | A1 | * | 7/2015 | Bosch .................... A61P 43/00 424/156.1 |
| 2020/0297860 | A1 | | 9/2020 | Albone et al. |
| 2021/0090062 | A1 | | 3/2021 | Wurmfeld |
| 2021/0238304 | A1 | | 8/2021 | Albone et al. |
| 2021/0299269 | A1 | | 9/2021 | Pazolli et al. |
| 2022/0081486 | A1 | | 3/2022 | Henry et al. |

FOREIGN PATENT DOCUMENTS

| | | | |
|---|---|---|---|
| CN | 101213297 A | 7/2008 | |
| CN | 101282967 A | 10/2008 | |
| CN | 107074827 A | 8/2017 | |
| RU | 2619208 C2 | 5/2017 | |
| WO | WO 2006/121168 A1 | 11/2006 | |
| WO | WO 2015/175594 A1 | 11/2015 | |
| WO | WO-2015175594 A1 * | 11/2015 | ......... A61K 31/4427 |
| WO | WO 2017/040526 A2 | 3/2017 | |
| WO | WO 2017/087667 A1 | 5/2017 | |
| WO | WO-2017087667 A1 * | 5/2017 | ......... A61K 31/4427 |
| WO | WO 2017/151979 A1 | 9/2017 | |
| WO | WO 2019/232433 A2 | 12/2019 | |

(Continued)

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*

(Continued)

*Primary Examiner* — Vanessa L. Ford
*Assistant Examiner* — Sandra Dillahunt
(74) *Attorney, Agent, or Firm* — Finnegan, Henderson, Farabow, Garrett & Dunner, LLP

(57) ABSTRACT

This disclosure relates to methods for the treatment of neoplastic disorders by administering Compound 1, or a pharmaceutically acceptably salt thereof, on its own and/or as part of a conjugate or composition, and inducing production of at least one neoantigen.

12 Claims, 1 Drawing Sheet

(56) References Cited

FOREIGN PATENT DOCUMENTS

| WO | WO 2019/232449 A9 | 12/2019 |
|---|---|---|
| WO | WO 2020/123836 A2 | 6/2020 |
| WO | WO 2021/090062 A1 | 5/2021 |
| WO | WO 2021/148003 A1 | 7/2021 |
| WO | WO 2021/248005 | 12/2021 |

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937. (Year: 1999).*
Heppner et al. Tumor heterogeneity: biological implications and therapeutic consequences. Cancer Metastasis Review 2:5-23; 1983 (Year: 1983).*
Sporn et al. Chemoprevention of Cancer, Carcinogenesis, vol. 21 (2000), 525-530 (Year: 2000).*
Auerbach et al. Angiogenesis assays: problems and pitfalls. Cancer and Metastasis Reviews, 2000, 19: 167-172 (Year: 2000).*
Gura T. Systems for Identifying New Drugs Are Often Faulty. Science, 1997, 278(5340): 1041-1042 (Year: 1997).*
Jain RK. Barriers to Drug Delivery in Solid Tumors. Scientific American, Jul. 1994,58-65 (Year: 1994).*
Hait. Anticancer drug development: the grand challenges. Nature Reviews/Drug Discovery, 2010, 9, pp. 253-254 (Year: 2010).*
Gravanis et al. The chagning world of cancer drug development: the regulatory bodies' perspective. Chin Clin Oncol, 2014, 3, pp. 1-5 (Year: 2014).*
Beans. PNAS 2018; 115(50): 12539-12543 (Year: 2018).*
Franzese et al., (2017) "Tumor immunotherapy: drug-induced neoantigens (xenogenization) and immune checkpoint inhibitors", Oncotarget, 8(25):41641-41669.
International Patent Application No. PCT/US2019/034992, filed May 31, 2019, Eisai R&D Management Co., Ltd.: International Search Report and Written Opinion, dated Dec. 17, 2019 (20 pages).
Chinese Patent Application No. 201980042241.3, filed May 31, 2019, by Eisai R&D Management Co., Ltd., Office Action and Search Report, dated Mar. 20, 2023.
Derksen et al., (2004) "Illegitimate WNT signaling promotes proliferation of multiple myeloma cells", *Proc Natl Acad Sci USA*, 101(16):6122-6127.
Dirks et al., (2008) "Brain tumor stem cells: bringing order to the chaos of brain cancer", *J Clin Oncol*, 26(17):2916-2924.
Fedyanin et al., (2018) "Some aspects of immunotherapy for colon cancer", *Pelvic Surgery and Oncology*, 8(1):19-27 (translation of annotation).
Lopez-Lazaro (2015) "The migration ability of stem cells can explain the existence of cancer of unknown primary site. Rethinking metastasis", *Oncoscience*, 2(5):467-475.
Marin-Acevedo et al., (2018) "Next generation of immune checkpoint therapy in cancer: new developments and challenges", *J Hemotol Oncol*, 11(1):39 (20 pages).
Russian Patent Application No. 2020143065, filed May 31, 2019, by Eisai R&D Management Cp., Ltd., Office Action dated Apr. 18, 2023.
Russian Patent Application No. 2020143065, filed May 31, 2019, by Eisai R&D Management Cp., Ltd., Search Report dated Apr. 18, 2023.
Tran et al., (2010) "Survival comparison between glioblastoma multiforme and other incurable cancers", *J Clin Neurosci*, 17(4):417-421.

* cited by examiner

METHODS OF USING SPLICING MODULATORS

The present disclosure claims the benefit of priority to U.S. Provisional Patent Application No. 62/679,696, filed Jun. 1, 2018; and U.S. Provisional Patent Application No. 62/679,699, filed Jun. 1, 2018. All of the aforementioned applications are incorporated herein by reference in their entirety.

The present disclosure relates to methods of treatment or diagnosis of cancers that are amenable to treatment by disruption of RNA splicing by administering Compound 1, or a pharmaceutically acceptable salt thereof. The present disclosure further relates to methods of treatment or diagnosis wherein a neoantigen is induced upon administration of Compound 1, or a pharmaceutically acceptable salt thereof.

The majority of protein-coding genes in the human genome are composed of multiple exons (coding regions) that are separated by introns (non-coding regions). Gene expression results in a single precursor messenger RNA (pre-mRNA). The intron sequences are subsequently removed from the pre-mRNA by a process called splicing, which results in the mature messenger RNA (mRNA). By including different combinations of exons, alternative splicing gives rise to mRNAs encoding distinct protein isoforms.

RNA splicing is catalyzed by the spliceosome, a dynamic multiprotein-RNA complex composed of five small nuclear RNAs (snRNAs U1, U2, U4, U5, and U6) and associated proteins. The spliceosome assembles on pre-mRNAs to establish a dynamic cascade of multiple RNA and protein interactions that catalyze excision of the introns and ligation of exons (Matera and Wang (2014) Nat Rev Mol Cell Biol. 15(2):108-21). Accumulating evidence has linked human diseases to dysregulation in RNA splicing that impact many genes (Scotti and Swanson (2016) Nat Rev Genet. 17(1): 19-32).

The spliceosome is an important target in cancer biology. Several studies have now documented significant alterations in the splicing profile of cancer cells, as well as in the splicing factors themselves (Agrawal et al. (2018) Curr Opin Genet Dev. 48:67-74). Alternative splicing can lead to differential exon inclusion/exclusion, intron retention, or usage of cryptic splice sites (Seiler et al. (2018) Cell Rep. 23(1):282-296). Altogether, these events account for functional changes that may contribute to tumorigenesis or resistance to therapy (Siegfried and Karni (2018) Curr Opin Genet Dev. 48:16-21).

Certain natural products and derivatives of the same can bind the SF3b spliceosome complex. (Exemplary natural products and derivatives of the same, such as certain pladienolide B compounds and related compounds, are disclosed in WO 2002/060890; WO 2004/011459; WO 2004/011661; WO 2004/050890; WO 2005/052152; WO 2006/009276; and WO 2008/126918.) These small molecules modulate splicing by promoting intron retention and/or exon skipping (Teng et al. (2017) Nat Commun. 8:15522). A significant portion of the resulting transcripts contain premature stop codons triggering nonsense mediated mRNA decay (NMD). Furthermore, because canonical splicing is impaired, canonical transcripts are considerably reduced, which can negatively impact cell function and viability. For this reason, splicing modulators have become a promising class of drugs for the treatment of cancer (Puthenveetil et al. (2016) Bioconjugate Chem. 27:1880-8).

It was previously shown that pladienolide pyridine compounds having Formula I, herein referred to as "Compound 1," and pharmaceutically acceptable salts thereof:

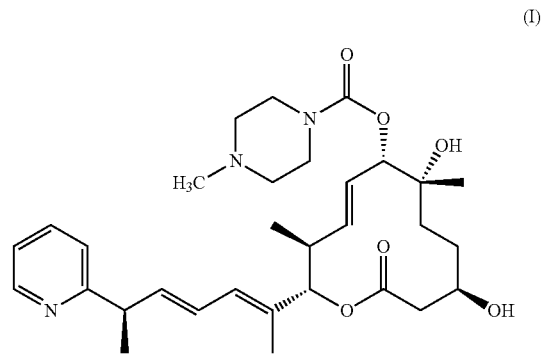 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C]

(I)

also known as, (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl4-methylpiperazine-1-carboxylate, demonstrate splicing modulator activity and cellular lethality in SF3b1 mutant cell lines. See, e.g., U.S. Pat. No. 9,481,669 B2 and International Application No. PCT/US2016/062525, all of which are incorporated by reference.

Immune checkpoint blockade (ICB) has recently proven to be a paradigm shift for the treatment of several different cancer types. However, not all patients demonstrate robust/durable responses to ICB. See, e.g., Zappasodi, R. et al. Emerging Concepts for Immune Checkpoint Blockade-Based Combination Therapies. *Cancer Cell* 33, 581-598, doi:10.1016/j.ccell.2018.03.005 (2018); and Wolchok, J. D. et al. Overall Survival with Combined Nivolumab and Ipilimumab in Advanced Melanoma. *N Engl J Med* 377, 1345-1356, doi:10.1056/NEJMoa1709684 (2017). Therefore, there exists a need to discover complementary therapeutic agents to administer in combination with ICB or any other therapy to improve and/or maximize patient response.

In various embodiments, the present disclosure provides, in part, pladienolide pyridine compounds with biological activity against neoplastic cells. The compounds may slow, inhibit, and/or reverse tumor growth in mammals, and may be useful for treating human cancer patients.

The present disclosure more specifically relates, in various embodiments, to Compound 1, or a pharmaceutically acceptable salt thereof, which is capable of binding and killing neoplastic cells.

In various embodiments, the present disclosure further relates to conjugates (e.g., antibody-drug conjugates (ADCs), peptide-drug conjugates (PDCs), etc.) that are capable of binding and delivering a cytotoxic agent, e.g., a compound disclosed herein, e.g., to kill targeted neoplastic cells. In various embodiments, the conjugates disclosed herein comprise a linker that attaches Compound 1, or a pharmaceutically acceptable salt thereof, to a cell-binding agent (e.g., an antibody, antigen binding fragment, peptide, receptor, receptor fragment, etc.).

In some embodiments, the conjugates disclosed herein may be represented by Formula II:

$$X\text{-}(L\text{-}D)_p \qquad (II)$$

wherein
X is a cell-binding agent which targets a neoplastic cell or another oncology-related target (e.g., an antigen expressed predominantly, exclusively, or preferentially on a cancer cell);
D is a Compound of Formula I (e.g., Compound 1, or a pharmaceutically acceptable salt thereof);
L is a linker which covalently attaches X to D; and
p is an integer from 1 to 15.

In some embodiments, the cell-binding agent for use in a conjugate (e.g., an antibody-drug conjugate) comprises or consists of an antibody or an antigen binding fragment thereof. In some embodiments, the conjugate is an antibody-drug conjugate (ADC). In some embodiments, the conjugate is an antibody-drug conjugate (ADC) of Formula II(a):

Ab-(L-D)$_p$    (II(a))

wherein
Ab is an antibody or an antigen binding fragment thereof which targets a neoplastic cell;
D is a Compound of Formula I (e.g., Compound 1, or a pharmaceutically acceptable salt thereof);
L is a linker which covalently attaches Ab to D; and
p is an integer from 1 to 15.

In some embodiments, the cell-binding agent for use in a conjugate (e.g., a peptide-drug conjugate) comprises or consists of a peptide (e.g., a linear or cyclic peptide). In some embodiments, the conjugate is a peptide-drug conjugate (PDC). In some embodiments, the conjugate is a peptide-drug conjugate (PDC) of Formula II(b):

P-(L-D)$_p$    (II(b))

wherein
P is a peptide which targets a neoplastic cell;
D is a Compound of Formula I (e.g., Compound 1, or a pharmaceutically acceptable salt thereof);
L is a linker which covalently attaches P to D; and
p is an integer from 1 to 15.

In some embodiments, the cell-binding agent for use in a conjugate comprises or consists of a receptor or a receptor fragment.

Other exemplary cell-binding agents for use in the disclosed conjugates (e.g., conjugates of Formula II) are also provided and described herein. For instance, in some embodiments, the cell-binding agent may comprise a DARPin, a duobody, a bicyclic peptide, a nanobody, a centyrin, MSH (melanocyte-stimulating hormone), a receptor-Fc fusion molecule, a T-cell receptor structure, a steroid hormone, a growth factor, or a colony-stimulating factor. In some embodiments, the cell-binding agent may comprise a non-antibody scaffold (e.g., a domain-sized scaffold or a constrained peptide).

In some embodiments, the linker used in a conjugate disclosed herein is stable outside a cell, such that the conjugate remains intact when present in extracellular conditions, but is capable of being cleaved, e.g., using a cleavable moiety in the linker connecting the cell-binding agent and the cytotoxic agent, upon internalization into a cell, e.g., a neoplastic cell. In some embodiments, Compound 1, or a pharmaceutically acceptable salt thereof, is cleaved from the cell-binding agent (e.g., an antibody, antigen binding fragment, peptide, receptor, or receptor fragment) when the conjugate enters a cell that expresses an antigen targeted by the cell-binding agent of the conjugate. In some embodiments, the linker is a cleavable linker. In other embodiments, Compound 1, or a pharmaceutically acceptable salt thereof, is released from the conjugate by degradation of the cell-binding agent and/or linker. In some embodiments, the linker is a non-cleavable linker.

In some embodiments, p is an integer from 1 to 15. In some embodiments, p is an integer from 1 to 10. In some embodiments, p is an integer from 1 to 8. In some embodiments, p is an integer from 1 to 4. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 2 to 3. In some embodiments, p is 1, 2, 3, 4, 5, 6, 7, or 8.

In some embodiments, provided herein is a method of inducing at least one neoantigen, comprising contacting a neoplastic cell with an effective amount of Compound 1, or a pharmaceutically acceptable salt thereof. In some embodiments, such contact may induce production of at least one neoantigen.

In some embodiments, provided herein is a method of inducing at least one neoantigen and/or a T-cell response in a subject having or suspected of having a neoplastic disorder, comprising administering to the subject an effective amount of Compound 1, or a pharmaceutically acceptable salt thereof.

In some embodiments, provided herein is a method of treating a subject having or suspected of having a neoplastic disorder. In certain embodiments, the method comprises administering to the subject an effective amount of Compound 1, or a pharmaceutically acceptable salt thereof. In some embodiments, administration of Compound 1, or a pharmaceutically acceptable salt thereof, induces at least one neoantigen and/or a T-cell response.

In some embodiments, the methods provided herein may further comprise administering at least one additional therapy. In some embodiments, the methods provided herein may result in lower systemic toxicity and/or improved tolerance.

In other embodiments, provided herein is a method of treating a subject having or suspect of having a neoplastic disorder. In some embodiments, the method comprises administering to the subject an effective amount of Compound 1, or a pharmaceutically acceptable salt thereof, wherein administration may result in inducing at least one neoantigen and/or a T-cell response. In some embodiments, the method may also comprise detecting one or more neoantigens and/or a T-cell response in the subject after administration of Compound 1, or a pharmaceutically acceptable salt thereof. In some embodiments, the method may also comprise continuing administration of Compound 1, or a pharmaceutically acceptable salt thereof, if one or more neoantigens and/or a T-cell response is detected.

In some embodiments, provided herein is a method of treating a subject having or suspected of having a neoplastic disorder, comprising administering to the subject an effective amount of Compound 1, or a pharmaceutically acceptable salt thereof.

In some embodiments of the methods provided herein, Compound 1, or a pharmaceutically acceptable salt thereof, is administered on its own or as a drug moiety of a conjugate (e.g., any of the exemplary conjugates disclosed herein). In some embodiments, Compound 1, or a pharmaceutically acceptable salt thereof, is administered as a composition comprising multiple copies of the compound or multiple copies of a conjugate comprising the compound. Such compositions are disclosed herein.

In some embodiments, provided herein is a neoantigen vaccine comprising at least one neoantigen peptide. In some embodiments, the at least one neoantigen peptide comprises a modified or novel neoantigen sequence induced by contacting a neoplastic cell with an effective amount of Compound 1, or a pharmaceutically acceptable salt thereof.

DETAILED DESCRIPTION OF ILLUSTRATIVE EMBODIMENTS

Figure 1A:
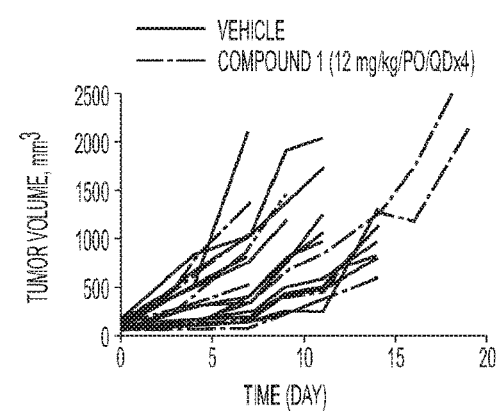
FIGS. 1A-1C show the antitumor effect of administration of Compound 1 as a sole monotherapy, an anti-CTLA4 antibody as a monotherapy, and Compound 1 and an anti-CTLA4 antibody as a combination therapy.
Figure 1A:
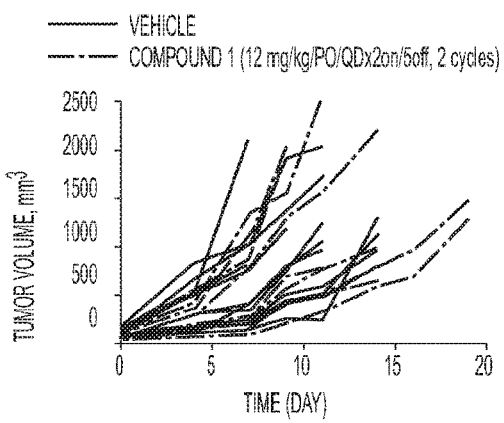
Figure 1A:
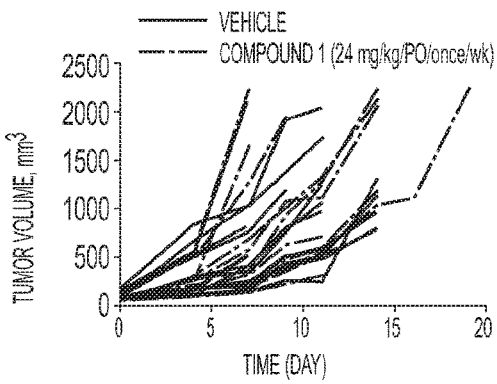

The disclosed compositions and methods may be understood more readily by reference to the following detailed description taken in connection with the accompanying figures, which form a part of this disclosure.

Throughout this text, the descriptions refer to compositions and methods of using the compositions. Where the disclosure describes or claims a feature or embodiment associated with a composition, such a feature or embodiment is equally applicable to the methods of using the composition. Likewise, where the disclosure describes or claims a feature or embodiment associated with a method of using a composition, such a feature or embodiment is equally applicable to the composition.

When a range of values is expressed, it includes embodiments using any particular value within the range. Further, reference to values stated in ranges includes each and every value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise. All references cited herein are incorporated by reference for any purpose. Where a reference and the specification conflict, the specification will control.

It is to be appreciated that certain features of the disclosed compositions and methods, which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly dictates otherwise.

The terms "about" or "approximately" in the context of numerical values and ranges refers to values or ranges that approximate or are close to the recited values or ranges such that the embodiment may perform as intended, such as having a desired amount of nucleic acids or polypeptides in a reaction mixture, as is apparent to the skilled person from the teachings contained herein. In some embodiments, about means plus or minus 10% of a numerical amount.

The term "conjugate," as used herein, refers to one or more therapeutic compounds (e.g., Compound 1, or a pharmaceutically acceptable salt thereof) linked to one or more cell-binding agents, and is defined by the generic formula: X-(L-D)$_p$ (Formula II), wherein X=a cell-binding agent, L=a linker moiety, D=a drug moiety (e.g., Compound 1, or a pharmaceutically acceptable salt thereof), and p=the number of drug moieties per cell-binding agent. In conjugates comprising a drug moiety of Compound 1, or a pharmaceutically acceptable salt thereof, "p" refers to the number of drug moieties linked to the cell-binding agent. An exemplary conjugate is a conjugate of Formula II:

wherein
X is a cell-binding agent which targets a neoplastic cell;
D is Compound 1, or a pharmaceutically acceptable salt thereof;
L is a linker which covalently attaches X to D; and
p is an integer from 1 to 15.

In some embodiments, the linker L is a cleavable linker. In some embodiments, the linker L can include a cleavable moiety between the cell-binding agent and the therapeutic compound. In some embodiments, the linker L can include a cleavable moiety that can be attached to either or both the cell-binding agent and the therapeutic compound by spacer unit(s). In some embodiments, when a spacer unit attaches the cleavable moiety to the therapeutic compound, it is a self-immolative spacer unit. In some embodiments, the linker L does not include a cleavable moiety, and is a non-cleavable linker. In some embodiments, the linker L can include at least one spacer unit that can directly attach to the cell-binding agent and to the therapeutic compound.

In some embodiments, the cell-binding agent X comprises an antibody or an antigen binding fragment thereof. In some embodiments, the cell-binding agent X comprises a peptide. In some embodiments, the cell-binding agent X comprises a receptor or a receptor fragment that interacts with an antigen, e.g., an antigen expressed exclusively, predominantly, or preferentially on a cancer cell.

As used herein, the term "cell-binding agent" refers to any agent that is capable of binding to an animal (e.g., human) cell and delivering a drug moiety (e.g., Compound 1, or a pharmaceutically acceptable salt thereof). The term encompasses antibodies and antigen binding fragments (e.g., monoclonal antibodies and fragments thereof such as Fabs and scFVs). The term further encompasses peptides and other exemplary cell-binding agents. For instance, in some embodiments, a cell-binding agent can be an antibody, an antigen binding fragment, a peptide, or any of a variety of non-antibody scaffolds (e.g., DARPins, duobodies, bicyclic peptides, nanobodies, centyrins, MSH (melanocyte-stimulating hormone), receptor-Fc fusion molecules, T-cell receptor structures, steroid hormones such as androgens and estrogens, growth factors, and colony-stimulating factors such as EGF). In some embodiments, the cell-binding agent comprises a DARPin, a duobody, a bicyclic peptide, a nanobody, a centyrin, MSH (melanocyte-stimulating hormone), a receptor-Fc fusion molecule, a T-cell receptor structure, a steroid hormone, a growth factor, or a colony-stimulating factor. In some embodiments, the cell-binding agent comprises a non-antibody scaffold. In some embodiments, non-antibody scaffolds can broadly fall into two structural classes, namely domain-sized compounds (approximately 6-20 kDa) and constrained peptides (approximately 2-4 kDa). Exemplary domain-sized scaffolds include but are not limited to affibodies, affilins, anticalins, atrimers, DARPins, FN3 scaffolds (e.g., adnectins and centyrins), fynomers, Kunitz domains, pronectins, 0-bodies, and receptor-Fc fusion proteins, whereas exemplary constrained peptides include avimers, bicyclic peptides, and Cys-knots. In some embodiments, the cell-binding agent comprises a domain-sized scaffold. In some embodiments, the cell-binding agent and/or domain-sized scaffold is an affibody, an affilin, an anticalin, an atrimer, a DARPin, a FN3 scaffold, a fynomer, a Kunitz domain, a pronectin, an O-body, or a receptor-Fc fusion protein. In some embodiments, the cell-binding agent comprises a constrained peptide. In some embodiments, the cell-binding agent and/or constrained peptide is an avimer, a bicyclic peptide, or a Cys-knot. Non-antibody scaffolds are reviewed, e.g., in Vazquez-Lombardi et al. (2015) Drug Dis Today 20(10):1271-83.

The terms "antibody-drug conjugate" and "ADC" are used interchangeably, and refer to one or more therapeutic compounds (e.g., Compound 1, or a pharmaceutically acceptable salt thereof) linked to one or more antibodies or antigen binding fragments, and is defined by the generic formula: A-(L-D)$_p$ (Formula II(a)), wherein Ab=an antibody or antigen binding fragment, L=a linker moiety, D=a drug moiety (e.g., Compound 1, or a pharmaceutically acceptable salt thereof), and p=the number of drug moieties per antibody or antigen binding fragment. In ADCs comprising a drug moiety of Compound 1, or a pharmaceutically acceptable salt thereof, "p" refers to the number of drug moieties linked to the antibody or antigen binding fragment. An exemplary ADC is an ADC of Formula II(a):

$$Ab\text{-}(L\text{-}D)_p \qquad (II(a))$$

wherein
Ab is an antibody or an antigen binding fragment thereof which targets a neoplastic cell;
D is Compound 1, or a pharmaceutically acceptable salt thereof;
L is a linker which covalently attaches Ab to D; and
p is an integer from 1 to 15.

In some embodiments, the linker L is a cleavable linker. In some embodiments, the linker L can include a cleavable moiety between the antibody or antigen binding fragment and the therapeutic compound. In some embodiments, the linker L can include a cleavable moiety that can be attached to either or both the antibody or antigen binding fragment and the therapeutic compound by spacer unit(s). In some embodiments, when a spacer unit attaches the cleavable moiety to the therapeutic compound, it is a self-immolative spacer unit. In some embodiments, the linker L does not include a cleavable moiety, and is a non-cleavable linker. In some embodiments, the linker L can include at least one spacer unit that can directly attach to the antibody or antigen binding fragment and to the therapeutic compound.

In some embodiments, the antibody or antigen binding fragment Ab is a four-chain antibody (also referred to as an immunoglobulin or a full-length or intact antibody), comprising two heavy chains and two light chains. In some embodiments, the antibody or antigen binding fragment Ab is a two-chain half body (one light chain and one heavy chain), or an antigen binding fragment of an immunoglobulin. In some embodiments, the antibody or antigen binding fragment Ab is an antigen binding fragment of an immunoglobulin that retains the ability to bind a target cancer antigen and/or provide a function of an immunoglobulin. In some embodiments, the antibody or antigen binding fragment Ab is able to bind a target cancer antigen with high specificity and high affinity. In some embodiments, the antibody or antigen binding fragment Ab is an internalizing antibody or internalizing antigen binding fragment thereof.

In some embodiments, the internalizing antibody or internalizing antigen binding fragment thereof binds to a target cancer antigen expressed on the surface of a cell and enters the cell upon binding. In some embodiments, Compound 1, or a pharmaceutically acceptable salt thereof, is released from the antibody or antigen binding fragment of the ADC after the ADC enters and is present in a cell expressing the target cancer antigen (i.e., after the ADC has been internalized), e.g., by cleavage, by degradation of the antibody or antigen binding fragment, or by any suitable release mechanism (e.g., enzymatic action, hydrolysis, oxidation).

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain ($V_H$) and a heavy chain constant region ($C_H$). The light chain is composed of a light chain variable domain ($V_L$) and a light chain constant domain ($C_L$). For the purposes of this application, the mature heavy chain and light chain variable domains each comprise three complementarity determining regions (CDR1, CDR2 and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', F(ab)$_2$, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity (e.g., binds the target antigen, internalizes within a target-antigen expressing cell).

The term "antigen binding fragment" or "antigen binding portion" of an antibody, as used herein, refers to one or more fragments of an antibody or protein that retain the ability to specifically bind to an antigen. Antigen binding fragments may also retain the ability to internalize into an antigen-expressing cell. In some embodiments, antigen binding fragments also retain immune effector activity. It has been shown that fragments of a full-length antibody can perform the antigen binding function of a full-length antibody. Examples of binding fragments encompassed within the term "antigen binding fragment" or "antigen binding portion" of an antibody include (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment, which comprises a single variable domain, e.g., a $V_H$ domain (see, e.g., Ward et al. (1989) Nature 341:544-6; and WO 1990/005144); and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). See, e.g., Bird et al. (1988) Science 242:423-6; and Huston et al. (1988) Proc Natl Acad Sci. USA 85:5879-83. Such single chain antibodies are also intended to be encompassed within the term "antigen binding fragment" or "antigen binding portion" of an antibody, and are known in the art as an exemplary type of binding fragment that can internalize into cells upon binding (see, e.g., Zhu et al. (2010) 9:2131-41; He et al. (2010) J Nucl Med. 51:427-32; and Fitting et al. (2015) MAbs 7:390-402). In certain embodiments, scFv molecules may be incorporated into a fusion protein. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc Natl Acad Sci. USA 90:6444-8; and Poljak et al. (1994) Structure 2:1121-3). Antigen binding fragments are obtained using conventional techniques known to those of skill in the art, and the binding fragments are screened for utility (e.g., binding affinity, internalization) in the same manner as are intact antibodies. Antigen binding fragments may be prepared by cleavage of the intact protein, e.g., by protease or chemical cleavage.

The terms "peptide-drug conjugate" and "PDC" are used interchangeably, and refer to one or more therapeutic compounds (e.g., Compound 1, or a pharmaceutically acceptable salt thereof) linked to one or more peptides, and is defined by the generic formula: P-(L-D)$_p$ (Formula II(b)), wherein P=a peptide (e.g., a linear or cyclic peptide), L=a linker moiety, D=a drug moiety (e.g., Compound 1, or a pharmaceutically acceptable salt thereof), and p=the number of drug moieties per peptide. In PDCs comprising a drug moiety of Compound 1, or a pharmaceutically acceptable salt thereof, "p" refers to the number of drug moieties linked to the peptide. An exemplary PDC is a PDC of Formula II(b):

P-(L-D)$_p$           (II(b))

wherein

P is a peptide which targets a neoplastic cell;

D is Compound 1, or a pharmaceutically acceptable salt thereof;

L is a linker which covalently attaches P to D; and p is an integer from 1 to 15.

In some embodiments, the linker L is a cleavable linker. In some embodiments, the linker L can include a cleavable moiety between the peptide and the therapeutic compound. In some embodiments, the linker L can include a cleavable moiety that can be attached to either or both the peptide and the therapeutic compound by spacer unit(s). In some embodiments, when a spacer unit attaches the cleavable moiety to the therapeutic compound, it is a self-immolative spacer unit. In some embodiments, the linker L does not include a cleavable moiety, and is a non-cleavable linker. In some embodiments, the linker L can include at least one spacer unit that can directly attach to the peptide and to the therapeutic compound.

In some embodiments, the peptide P is able to bind a target cancer antigen with high specificity and high affinity. In some embodiments, the target cancer antigen targeted by the peptide is expressed on the cell surface and not within the cytosol or nucleus. In some embodiments, the peptide P is a linear peptide. In some embodiments, the peptide P is a cyclic peptide. In some embodiments, the peptide P is less than about 250, about 200, about 150, about 100, about 50, about 30, about 20, about 10, or about 5 amino acids in length. In some embodiments, the peptide P is less than about 100, about 50, about 30, about 20, about 10, or about 5 amino acids in length.

As used herein, the term "peptide" refers to a polymer of amino acid residues. The term encompasses amino acid polymers comprising two or more amino acids joined to each other by peptide bonds, amino acid polymers in which one or more amino acid residues is an artificial chemical mimetic of a corresponding naturally-occurring amino acid, as well as naturally-occurring amino acid polymers and non-naturally-occurring amino acid polymers. The term includes, for example, biologically active fragments, substantially homologous polypeptides, oligopeptides, homodimers, heterodimers, variants of polypeptides, modified polypeptides, derivatives, analogs, fusion proteins, among others. The terms also include natural peptides, recombinant peptides, synthetic peptides, or a combination thereof.

"Internalizing" as used herein in reference to a cell-binding agent (e.g., an antibody, antigen binding fragment, peptide, receptor, or receptor fragment) refers to a cell-binding agent that is capable of being taken through the cell's lipid bilayer membrane to an internal compartment (i.e., "internalized") upon binding to the cell, preferably into a degradative compartment in the cell. In some embodiments, the cell-binding agent used in the conjugates disclosed herein targets a cell surface antigen and is an internalizing cell-binding agent (i.e., the conjugate transfers through the cellular membrane after antigen binding). In some embodiments, the internalizing cell-binding agent binds a receptor on the cell surface. An internalizing cell-binding agent that targets a receptor on the cell membrane may induce receptor-mediated endocytosis. In some embodiments, the internalizing cell-binding agent is taken into the cell via receptor-mediated endocytosis.

"Non-internalizing" as used herein in reference to a cell-binding agent (e.g., an antibody, antigen binding fragment, peptide, receptor, or receptor fragment) refers to a cell-binding agent that remains at the cell surface upon binding to the cell. In some embodiments, the cell-binding agent used in the conjugates disclosed herein targets a cell surface antigen and is a non-internalizing cell-binding agent (i.e., the conjugate remains at the cell surface and does not transfer through the cellular membrane after antigen binding). In some embodiments, the non-internalizing cell-binding agent binds a non-internalizing receptor or other cell surface antigen. Exemplary non-internalizing cell surface antigens include but are not limited to CA125 and CEA, and cell-binding agents that bind to non-internalizing antigen targets are also known in the art (see, e.g., Bast et al. (1981) J Clin Invest. 68(5):1331-7; Scholler and Urban (2007) Biomark Med. 1(4):513-23; and Boudousq et al. (2013) PLoS One 8(7):e69613).

A "linker" or "linker moiety" is used herein to refer to any chemical moiety that is capable of covalently joining a compound, usually a drug moiety such as Compound 1, or a pharmaceutically acceptable salt thereof, to another moiety such as a cell-binding agent (e.g., an antibody, antigen binding fragment, peptide, receptor, or receptor fragment). Linkers can be susceptible to or substantially resistant to peptidase-induced cleavage, acid-induced cleavage, light-based cleavage, esterase-induced cleavage, and/or disulfide bond cleavage, at conditions under which the compound and/or the cell-binding agent remains active. For instance, a linker may be "cleavable" or "non-cleavable" (Ducry and Stump (2010) Bioconjugate Chem. 21:5-13). Cleavable linkers are designed to release the drug moiety (e.g., Compound 1, or a pharmaceutically acceptable salt thereof) when subjected to certain environment factors, e.g., when internalized into the target cell, whereas non-cleavable linkers generally rely on the degradation of the cell-binding agent itself.

In some embodiments, the linker is a non-cleavable linker. In some embodiments, the drug moiety of a conjugate disclosed herein (e.g., Compound 1, or a pharmaceutically acceptable salt thereof) is released by degradation of the cell-binding agent. Non-cleavable linkers tend to remain covalently associated with at least one amino acid of the cell-binding agent and the drug upon internalization by and degradation within the target cell. Exemplary non-cleavable linkers may comprise thioether, cyclohexyl, N-succinimidyl 4-(N-maleimidomethyl) cyclohexane-1 carboxylate (SMCC), N-hydroxysuccinimide (NHS), one or more polyethylene glycol (PEG) moieties, or one or more alkyl moieties.

In some embodiments, the linker is a cleavable linker. A cleavable linker refers to any linker that comprises a cleavable moiety. As used herein, the term "cleavable moiety" refers to any chemical bond that can be cleaved. Suitable cleavable chemical bonds are well known in the art and include, but are not limited to, protease/peptidase labile bonds, acid labile bonds, photolabile bonds, disulfide bonds, and esterase labile bonds. Linkers comprising a cleavable moiety can allow for the release of the drug moiety (e.g., Compound 1, or a pharmaceutically acceptable salt thereof) from the conjugate via cleavage at a particular site in the linker. In some embodiments, the linker and/or cleavable moiety comprises a cleavable peptide moiety, i.e., any chemical bond linking amino acids (natural or synthetic amino acid derivatives) that can be cleaved by an agent that is present in the intracellular environment.

In some embodiments, the linker is cleavable under intracellular conditions, such that cleavage of the linker sufficiently releases the drug moiety (e.g., Compound 1, or a pharmaceutically acceptable salt thereof) from the cell-binding agent in the intracellular environment to activate the drug and/or render the drug therapeutically effective. In some embodiments, the drug moiety is not cleaved from the cell-binding agent until the conjugate enters a cell that expresses an antigen specific for the cell-binding agent of the conjugate, and the drug moiety is cleaved from the cell-binding agent upon entering the cell. In some embodiments, the linker comprises a cleavable moiety that is positioned such that no part of the linker or the cell-binding agent remains bound to the drug moiety upon cleavage. Exemplary cleavable linkers include protease/peptidase-sensitive linkers, pH-sensitive linkers (e.g., acid labile and/or hydrolyzable linkers), photolabile linkers, dimethyl-, disulfide-, or sulfonamide-containing linkers.

In some embodiments, the linker may be a dendritic type linker for covalent attachment of more than one drug moiety (e.g., Compound 1, or a pharmaceutically acceptable salt thereof) to a cell-binding agent through a branching, multifunctional linker moiety. See, e.g., Sun et al. (2002) Bioorg Med Chem Lett. 12:2213-5; and Sun et al. (2003) Bioorg Med Chem. 11:1761-8. Dendritic linkers can increase the molar ratio of drug to cell-binding agent, i.e., drug loading, which is related to the potency of the conjugate. Thus, where a cell-binding agent bears only one reactive cysteine thiol group, for example, a multitude of drug moieties may be attached through a dendritic linker. In some embodiments, the linker moiety or linker-drug moiety may be attached to the cell-binding agent via reduced disulfide bridging chemistry or limited lysine utilization technology. See, e.g., WO 2013/173391 and WO 2013/173393.

WO 2017/151979, US 2017/0252458, and US 2018/0193478 provide and are incorporated herein by reference for all exemplary linkers, exemplary linker attachment points to cell-binding agents (e.g., antibodies), and exemplary cell-binding agents (e.g., antibodies).

In some embodiments, the linker in any of the conjugates disclosed herein may comprise at least one spacer unit joining the cell-binding agent to the drug moiety (e.g., Compound 1, or a pharmaceutically acceptable salt thereof). In some embodiments, a spacer unit between the cell-binding agent and the cleavable moiety, when present, joins a cleavage site (e.g., a cleavable peptide moiety) in the linker to the cell-binding agent. In some embodiments, a spacer unit between the drug moiety and the cleavable moiety, when present, joins a cleavage site (e.g., a cleavable peptide moiety) in the linker to the drug moiety. In some embodiments, no cleavage site is present, and the spacer unit is used to link the cell-binding agent to the drug moiety.

A spacer unit may be "self-immolative" or "non-self-immolative." A "non-self-immolative" spacer unit is one in which part or all of the spacer unit remains bound to the drug moiety (e.g., Compound 1, or a pharmaceutically acceptable salt thereof) upon cleavage of the linker. Examples of non-self-immolative spacer units include, but are not limited to, a glycine spacer unit and a glycine-glycine spacer unit. Non-self-immolative spacer units may eventually degrade over time but do not readily release a linked native drug moiety entirely under cellular conditions. A "self-immolative" spacer unit allows for release of the native drug moiety under intracellular conditions. A "native drug" or "native drug moiety" is one where no part of the spacer unit or other chemical modification remains after cleavage/degradation of the spacer unit.

Drug loading is represented by p. The term "p" or "drug loading" refers to the number of drug moieties per cell-binding agent, i.e., the number of -L-D moieties per cell-binding agent (X), e.g., in conjugates of Formula II. The term may also refer to the number of L-D moieties per antibody or antigen binding fragment (Ab), e.g., in ADCs of Formula II(a), or to the number of L-D moieties per peptide (P), e.g., in PDCs of Formula II(b). For example, in conjugates of Formula II, if two compounds (e.g., two compounds each having the structure of Compound 1, or a pharmaceutically acceptable salt thereof) are linked to a cell-binding agent, p=2. In some embodiments, p is an integer from 1 to 15. In some embodiments, p is an integer from 1 to 10, 1 to 8, or 1 to 4. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 2 to 3. In some embodiments, p is 1, 2, 3, 4, 5, 6, 7, or 8.

In compositions comprising multiple copies of conjugates, e.g., conjugates of Formula II, "average p" refers to the average number of -L-D moieties per cell-binding agent, also referred to as "average drug loading."

The term "chemotherapeutic agent" or "anti-cancer agent" is used herein to refer to all agents that are effective in treating cancer regardless of mechanism of action. Inhibition of metastasis or angiogenesis is frequently a property of a chemotherapeutic agent. Chemotherapeutic agents include antibodies, biological molecules, and small molecules, and encompass the splicing modulator compounds described herein. A chemotherapeutic agent may be a cytotoxic or cytostatic agent. The term "cytostatic agent" refers to an agent that inhibits or suppresses cell growth and/or multiplication of cells. The term "cytotoxic agent" refers to a substance that causes cell death primarily by interfering with a cell's expression activity and/or functioning.

The term "Compound 1" or "Compound 1, or a pharmaceutically acceptable salt thereof," as used herein, refers to at least one entity chosen from compounds of Formula I and pharmaceutically acceptable salts thereof. Furthermore, unless otherwise stated, "Compounds of Formula I" may be one or more of the enantiomeric, diastereomeric, and/or geometric (or conformational) forms of the compound(s); for example, the R and S configurations for each asymmetric center, (Z) and (E) double bond isomers, and (Z) and (E) conformational isomers. Unless otherwise stated, compounds depicted herein coexisting with tautomeric forms are within the scope of the disclosure. Additionally, unless otherwise stated, structures depicted herein are also meant to include compounds that differ only in the presence of one or more isotopically enriched atoms. For example, compounds having the depicted structures except for the replacement of hydrogen by deuterium or tritium, or the replacement of a carbon by a $^{13}$C- or $^{14}$C-enriched carbon are within the scope of this disclosure. Such compounds may be useful, for example, as analytical tools or probes in biological assays.

Formula I may be represented by the following:

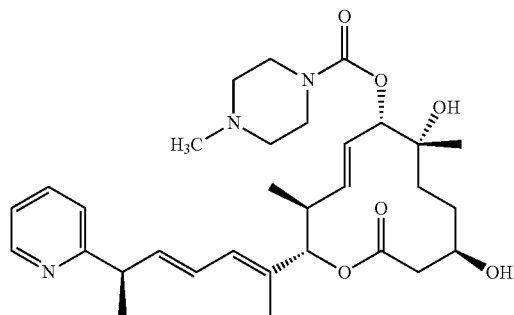 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C]

and/or the chemical name (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate.

The term "inhibit" or "inhibition of," as used herein, means to reduce by a measurable amount, and can include but does not require complete prevention or inhibition.

The terms "neoplastic disorder" and "cancer" are used herein interchangeably to refer to the presence of cells possessing characteristics typical of cancer-causing cells, such as uncontrolled proliferation, immortality, metastatic potential, rapid growth and proliferation rate, and/or certain morphological features. Often, cancer cells can be in the form of a tumor or mass, but such cells may exist alone within a subject, or may circulate in the blood stream as independent cells, such as leukemic or lymphoma cells. The terms "neoplastic disorder" and "cancer" includes all types of cancers and cancer metastases, including hematological malignancy, solid tumors, sarcomas, carcinomas and other solid and non-solid tumor cancers. Hematological malignancies may include B-cell malignancies, cancers of the blood (leukemias), cancers of plasma cells (myelomas, e.g., multiple myeloma), or cancers of the lymph nodes (lymphomas). Exemplary B-cell malignancies include chronic lymphocytic leukemia (CLL), follicular lymphoma, mantle cell lymphoma, and diffuse large B-cell lymphoma. Leukemias may include acute lymphoblastic leukemia (ALL), acute myelogenous leukemia (AML), chronic lymphocytic leukemia (CLL), chronic myelogenous leukemia (CML), chronic myelomonocytic leukemia (CMML), acute monocytic leukemia (AMoL), etc. Lymphomas may include Hodgkin's lymphoma and non-Hodgkin's lymphoma. Other hematologic malignancies may include myelodysplasia syndrome (MDS). Solid tumors may include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

The terms "tumor" and "neoplasm" refer to any mass of tissue that results from excessive cell growth or proliferation, either benign or malignant, including precancerous lesions.

The terms "tumor cell" and "neoplastic cell" are used interchangeably and refer to individual cells or the total population of cells derived from a tumor or neoplasm, including both non-tumorigenic cells and cancer stem cells. As used herein, the term "tumor cell" will be modified by the term "non-tumorigenic" when referring solely to those tumor cells lacking the capacity to renew and differentiate to distinguish those tumor cells from cancer stem cells.

The terms "subject" and "patient" are used interchangeably herein to refer to any animal, such as any mammal, including but not limited to, humans, non-human primates, rodents, and the like. In some embodiments, the mammal is a mouse. In some embodiments, the mammal is a human. In some embodiments, the subject is a mouse. In some embodiments, the subject is a human.

The term "co-administration" or administration "in combination with" one or more therapeutic agents includes concurrent administration and consecutive administration in any order.

A "pharmaceutical composition" refers to a preparation which is in such form as to permit administration and subsequently provide the intended biological activity of the active ingredient(s) and/or to achieve a therapeutic effect, and which contains no additional components which are unacceptably toxic to a subject to which the formulation would be administered. The pharmaceutical composition may be sterile.

A "pharmaceutical excipient" comprises a material such as an adjuvant, a carrier, pH-adjusting and buffering agents, tonicity adjusting agents, wetting agents, preservative, and the like.

"Pharmaceutically acceptable" means approved or approvable by a regulatory agency of the Federal or a state government, or listed in the U.S. Pharmacopeia or other generally recognized pharmacopeia, for use in animals, and more particularly in humans A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al. "Commentary: Occurrence of Pharmaceutically Acceptable Anions and Cations in the Cambridge Structural Database," J Pharmaceutical Sciences, vol. 94, no. 10 (2005), and Berge et al. "Pharmaceutical Salts," J Pharmaceutical Sciences, vol. 66, no. 1 (1977), which are incorporated by reference herein.

The term "effective amount," as used herein, refers to the amount of Compound 1, or a pharmaceutically acceptable salt thereof, described herein that is sufficient to perform a specifically stated purpose, for example to produce a therapeutic effect after administration, such as a reduction in tumor growth rate or tumor volume, a reduction in a symptom of cancer, or some other indicia of treatment efficacy. An effective amount can be determined in a routine manner in relation to the stated purpose. The term "therapeutically effective amount" refers to an amount of Compound 1, or a pharmaceutically acceptable salt thereof, described herein effective for detectable killing, reduction, and/or inhibition of the growth or spread of tumor cells, the size or number of tumors, and/or other measure of the level, stage, progression and/or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., inhibition of cell growth. The specific dose may vary depending on, for example, the particular pharmaceutical composition, the subject and their age and existing health conditions or risk for health conditions, the dosing regimen to be followed, the severity of the disease, whether it is administered in combination with other agents, timing of administration, the tissue to which it is administered, and the physical delivery system in which it is carried. In the case of cancer, a therapeutically effective amount of Compound 1, or a pharmaceutically acceptable salt thereof, can reduce the number of cancer cells, reduce tumor size, inhibit (e.g., slow or stop) tumor metastasis, inhibit (e.g., slow or stop) tumor growth, and/or relieve one or more symptoms.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "to treat" or "therapeutic" and grammatically related terms, refer to any improvement of any consequence of disease, such as prolonged survival, less morbidity, and/or a lessening of side effects which result from an alternative therapeutic modality. As is readily appreciated in the art, full eradication of disease is encompassed but not required for a treatment act. "Treatment" or "treat," as used herein, refers to the administration of a herein described Compound 1, or a pharmaceutically acceptable salt thereof, to a subject, e.g., a patient. The treatment can be to cure, heal, alleviate, relieve, alter, remedy, ameliorate, palliate, improve or affect the disorder, the symptoms of the disorder or the predisposition toward the disorder, e.g., a cancer. In some embodiments, in addition to treating a subject with a condition, a composition disclosed herein can also be provided prophylactically to prevent or reduce the likelihood of developing that condition.

Neoantigens and Methods of Use

Disclosed herein, in various embodiments, are methods of treating a patient by inducing neoantigens in tumor cells that can be targeted by the patient's immune system for clearance. Without being bound by theory, in various embodiments, administering Compound 1, or a pharmaceutically acceptable salt thereof, alone and/or as part of a conjugate or composition, may produce neoantigens that induce an immune response, induce a double-stranded RNA immune response, e.g., as a result of re-expressed intron-resident endogenous retroviruses, and/or produce neoantigens that induce immunogenic cell death.

As used herein, the term "neoantigen" refers to any antigen to which the immune system has not previously been exposed that arises from one or more tumor-specific mutations. Tumor-specific mutations can include missense mutations, frameshifts, translocations, and mRNA splicing variants, as well as mutations that influence posttranslational processing, such as phosphorylation and glycosylation. These exemplary mutations, in various embodiments, can be derived from non-synonymous coding changes and/or mutations that alter mRNA processing (e.g., splicing). All of these exemplary mutations, in various embodiments, can result in molecular changes that can be discriminated by an appropriate T-cell receptor. In various preferred embodiments, an exemplary neoantigen is a neoantigen induced by delivery of Compound 1, or a pharmaceutically acceptable salt thereof, alone and/or as part of a conjugate or composition. In various embodiments, delivery of Compound 1, or a pharmaceutically acceptable salt thereof, alone and/or as part of a conjugate or composition, can induce novel mRNA splicing that results in the translation of proteins representing neoantigens to which the immune system has not previously been exposed. A neoantigen may occur naturally or be induced by an agent, e.g., a splice modulator. In various embodiments, tumor-specific mutations may be mRNA splicing variants resulting from delivery or administration of Compound 1, or a pharmaceutically acceptable salt thereof, alone and/or as part of a conjugate or composition.

Without being bound by theory, in various embodiments, the administration of Compound 1, or a pharmaceutically acceptable salt thereof, alone and/or as part of a conjugate or composition, may induce mRNA splicing that results in the translation of proteins representing neoantigens recognized by the immune system as foreign. These can be targeted, e.g., by T-cells, resulting in an amplified host response against the tumor cells in which the neoantigens are produced. Also, without being bound by theory, in various embodiments, the delivery of Compound 1, or a pharmaceutically acceptable salt thereof, alone and/or as part of a conjugate or composition, may cause the re-expression of intron-resident endogenous retroviruses, leading to a double-stranded RNA immune response. Further, without being bound by theory, in various embodiments, the delivery of Compound 1, or a pharmaceutically acceptable salt thereof, alone and/or as part of a conjugate or composition, may lead to immunogenic cell death triggered by Compound 1-induced release of mutationally-derived neoantigens. In various embodiments, the delivery of Compound 1, or a pharmaceutically acceptable salt thereof, alone and/or as part of a conjugate or composition, may induce a double-stranded RNA immune response. In various embodiments, the double-stranded RNA immune response can result from the re-expression of intron-resident endogenous retroviruses. In various embodiments, the double-stranded RNA immune response can result in tumor cell death. In various embodiments, the delivery of Compound 1, or a pharmaceutically acceptable salt thereof, alone and/or as part of a conjugate or composition, may induce immunogenic cell death. In various embodiments, the immunogenic cell death can result from release of mutational-derived neoantigens and/or a host immune response against tumor cells.

Accordingly, in various embodiments, methods of treatment are disclosed comprising inducing neoantigens by administering Compound 1, or a pharmaceutically acceptable salt thereof. In various embodiments, the method comprises administering a reduced dosage of Compound 1, or a pharmaceutically acceptable salt thereof, as compared to the dosage that would be needed absent the induction of neoantigens. In some embodiments, the method comprises administering one or more initial induction doses to produce neoantigens and induce an immune response (e.g., converting naïve T-cells to memory cells), followed by a reduced dosage or administration frequency (i.e., because of the combinatorial effect of Compound 1, or a pharmaceutically acceptable salt thereof, and of immune targeting of the neoantigens). In some embodiments, treatment can comprise a combination of administering Compound 1, or a pharmaceutically acceptable salt thereof, to induce a neoantigen-based immune response and at least one additional therapy (e.g., a second anti-cancer therapy). For example, in some embodiments, treatment can comprise a combination of administering Compound 1, or a pharmaceutically acceptable salt thereof, to induce a neoantigen-based immune response and one or more checkpoint inhibitors. In some embodiments, treatment can comprise a combination of administering Compound 1, or a pharmaceutically acceptable salt thereof, to induce a neoantigen-based immune response and one or more cytokines or cytokine analogs. In some embodiments, treatment can comprise a combination of administering Compound 1, or a pharmaceutically acceptable salt thereof, to induce a neoantigen-based immune response and one or more neoantigen vaccines. In some other embodiments, treatment can comprise a combination of administering Compound 1, or a pharmaceutically acceptable salt thereof, to induce a neoantigen-based immune response and engineered tumor-targeting T-cells (e.g., CAR-T).

In some embodiments, neoantigens can be used to monitor the effectiveness of treatment with Compound 1, or a pharmaceutically acceptable salt thereof. For instance, after administration of Compound 1, or a pharmaceutically acceptable salt thereof, a patient sample (e.g., a tumor biopsy) can be obtained and screened for neoantigens or for identifiers of an immune or inflammatory response. Further treatment can be provided, e.g., at reduced dosage, if a neoantigen and/or immune response is detected.

In various embodiments, methods of treatment are disclosed comprising inducing a double-stranded RNA immune response by administering Compound 1, or a pharmaceutically acceptable salt thereof.

In various embodiments, methods of treatment are disclosed comprising inducing immunogenic cell death by administering Compound 1, or a pharmaceutically acceptable salt thereof.

In various embodiments, administration of Compound 1, or a pharmaceutically acceptable salt thereof, can be combined with any known anti-cancer therapy. Examples of current immune activating strategies available for oncology treatment include, but are not limited to, treatment with immune checkpoint inhibitor (ICI) molecules, treatment with cytokines or cytokine analogs, vaccination with tumor-associated vaccines, and engineering tumor-targeting T-cells (e.g., expansion of tumor-infiltrating lymphocytes or CAR-T). These technologies are predominantly focused on enhancing or inducing an immune response to already existing tumor antigens (either mutations or aberrant expression of cell-surface proteins). One or more of these strategies may involve one or more mutations that are capable of inducing an antigenic T-cell response. For example, patient responses to checkpoint inhibition may correlate with non-synonymous mutational burden. In addition, cancer vaccine approaches may be used that rely on pre-existing mutations and the antigenicity of these mutations.

Compound 1, or a pharmaceutically acceptable salt thereof, may induce broad-ranging changes in the transcriptome that occur in multiple lineages. Translation of these mRNA changes may produce robust and reproducible protein changes that produce MHC1-bound neopeptides with high affinity across multiple HLA isotypes. Without being bound by theory, due to the large number of changes to the transcriptome and proteome, treatment with Compound 1, or a pharmaceutically acceptable salt thereof, may enrich the number of potentially reactive neoantigens for enhanced engagement of the adaptive immune response.

In various embodiments of the methods described herein, Compound 1, or a pharmaceutically acceptable salt thereof, is administered on its own. In various embodiments of the methods described herein, Compound 1, or a pharmaceutically acceptable salt thereof, is administered as part of a conjugate or composition, e.g., a pharmaceutical composition comprising Compound 1, or a pharmaceutically acceptable salt thereof, and a pharmaceutically acceptable carrier. In various embodiments, Compound 1, or a pharmaceutically acceptable salt thereof, is administered as a composition (e.g., a pharmaceutical composition) comprising multiple copies of the compound. In various embodiments, Compound 1, or a pharmaceutically acceptable salt thereof, is administered as a composition (e.g., a pharmaceutical composition) comprising multiple copies of one or more conjugates carrying the compound. In various embodiments, Compound 1, or a pharmaceutically acceptable salt thereof, is administered as an antibody-drug conjugate, a peptide-drug conjugate, or any of the exemplary conjugates disclosed herein.

In various embodiments of the methods described herein, Compound 1, or a pharmaceutically acceptable salt thereof, is administered as part of a conjugate.

In some embodiments, the conjugate is a conjugate of Formula II:

$$X\text{-}(L\text{-}D)_p \qquad (II)$$

wherein
X is a cell-binding agent which targets a neoplastic cell;
D is Compound 1, or a pharmaceutically acceptable salt thereof;
L is a linker which covalently attaches X to D; and
p is an integer from 1 to 15.

In some embodiments, the cell-binding agent comprises an antibody or an antigen binding fragment thereof. In some embodiments, the conjugate is an antibody-drug conjugate. In some embodiments, the conjugate is an antibody-drug conjugate of Formula II(a):

$$Ab\text{-}(L\text{-}D)_p \qquad (II(a))$$

wherein
Ab is an antibody or an antigen binding fragment thereof which targets a neoplastic cell;
D is Compound 1, or a pharmaceutically acceptable salt thereof;
L is a linker which covalently attaches Ab to D; and
p is an integer from 1 to 15.

In some embodiments, the cell-binding agent comprises a peptide. In some embodiments, the conjugate is a peptide-drug conjugate. In some embodiments, the conjugate is a peptide-drug conjugate of Formula II(b):

$$P\text{-}(L\text{-}D)_p \qquad (II(b))$$

wherein
P is a peptide which targets a neoplastic cell;
D is Compound 1, or a pharmaceutically acceptable salt thereof;
L is a linker which covalently attaches P to D; and
p is an integer from 1 to 15.

In some embodiments, the cell-binding agent comprises a DARPin, a duobody, a bicyclic peptide, a nanobody, a centyrin, MSH (melanocyte-stimulating hormone), a receptor-Fc fusion molecule, a T-cell receptor structure, a steroid hormone, a growth factor, or a colony-stimulating factor. In some embodiments, the cell-binding agent comprises a non-antibody scaffold. In some embodiments, the non-antibody scaffold comprises a domain-sized scaffold or a constrained peptide. In some embodiments, the domain-sized scaffold is an affibody, an affilin, an anticalin, an atrimer, a DARPin, a FN3 scaffold, a fynomer, a Kunitz domain, a pronectin, an O-body, or a receptor-Fc fusion protein. In some embodiments, the constrained peptide is an avimer, a bicyclic peptide, or a Cys-knot.

In some embodiments, L is a cleavable linker. In some embodiments, L is a non-cleavable linker. In some embodiments, p is an integer from 1 to 10. In some embodiments, p is an integer from 1 to 8. In some embodiments, p is an integer from 1 to 4.

Immune Induction and Treatment Regimen:

In various embodiments, the present disclosure provides a method of inducing at least one neoantigen by contacting a neoplastic cell with an effective amount of Compound 1, or a pharmaceutically acceptable salt thereof. In various embodiments, the present disclosure provides a method of inducing a double-stranded RNA immune response by contacting a neoplastic cell with an effective amount of Compound 1, or a pharmaceutically acceptable salt thereof. In various embodiments, the present disclosure provides a method of inducing immunogenic cell death by contacting a neoplastic cell with an effective amount of Compound 1, or a pharmaceutically acceptable salt thereof. In various embodiments, Compound 1, or a pharmaceutically acceptable salt thereof, is administered on its own and/or as part of a conjugate or composition.

In some embodiments, the neoplastic cell is present in an in vitro cell culture. In some embodiments, the neoplastic cell is obtained from a subject. In some embodiments, the neoplastic cell is present in a subject. In some embodiments, the neoplastic cell is derived from a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer (e.g., HER2-positive breast cancer), gastric cancer (e.g., gastric adenocarcinoma), prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

In various embodiments, the present disclosure further provides a method of inducing at least one neoantigen and/or a T-cell response in a subject having or suspected of having a neoplastic disorder by administering to the subject an effective amount of Compound 1, or a pharmaceutically acceptable salt thereof. Also provided herein, in various embodiments, is a method of treating a subject having or suspected of having a neoplastic disorder by administering to the subject an effective amount of Compound 1, or a pharmaceutically acceptable salt thereof, wherein administration of the Compound 1, or a pharmaceutically acceptable salt thereof, induces at least one neoantigen and/or a T-cell response. In various embodiments, Compound 1, or a pharmaceutically acceptable salt thereof, is administered on its own and/or as part of a conjugate or composition.

In various other embodiments, the present disclosure provides a method of inducing a double-stranded RNA immune response in a subject having or suspected of having a neoplastic disorder by administering to the subject an effective amount of Compound 1, or a pharmaceutically acceptable salt thereof. Also provided herein, in various embodiments, is a method of treating a subject having or suspected of having a neoplastic disorder by administering to the subject an effective amount of Compound 1, or a pharmaceutically acceptable salt thereof, wherein administration of the Compound 1, or a pharmaceutically acceptable salt thereof, induces a double-stranded RNA immune response. In various embodiments, Compound 1, or a pharmaceutically acceptable salt thereof, is administered on its own and/or as part of a conjugate or composition.

In still other embodiments, the present disclosure provides a method of inducing immunogenic cell death in a subject having or suspected of having a neoplastic disorder by administering to the subject an effective amount of Compound 1, or a pharmaceutically acceptable salt thereof. Further provided herein, in various embodiments, is a method of treating a subject having or suspected of having a neoplastic disorder by administering to the subject an effective amount of Compound 1, or a pharmaceutically acceptable salt thereof, wherein administration of the Compound 1, or a pharmaceutically acceptable salt thereof, induces immunogenic cell death. In various embodiments, Compound 1, or a pharmaceutically acceptable salt thereof, is administered on its own and/or as part of a conjugate or composition.

In some embodiments of the therapeutic methods described herein, the amount of Compound 1, or a pharmaceutically acceptable salt thereof, administered is reduced due to induction of at least one neoantigen and/or a T-cell response, relative to a standard dosage of Compound 1, or a pharmaceutically acceptable salt thereof. In some embodiments, the administered amount of Compound 1, or a pharmaceutically acceptable salt thereof, is reduced by 10%, 15%, 20%, 25%, 30%, 35%, 40%, 45%, 50%, 75%, or 90%, relative to a standard dosage of Compound 1, or a pharmaceutically acceptable salt thereof. In some embodiments, Compound 1, or a pharmaceutically acceptable salt thereof, is administered at least 10%, 15%, 20%, 25%, 30%, 35%, 40%, 45%, 50%, 75%, or 90% less frequently, relative to a standard dosing regimen of Compound 1, or a pharmaceutically acceptable salt thereof. In some embodiments, the administered amount and/or dosage of Compound 1, or a pharmaceutically acceptable salt thereof, results in lower systemic toxicity and/or improved tolerance.

In some embodiments, the methods described herein may further comprise administering at least one additional therapy (e.g., a checkpoint inhibitor, a neoantigen vaccine, a cytokine or cytokine analog, CAR-T, etc.). In some embodiments, the amount of Compound 1, or a pharmaceutically acceptable salt thereof, and/or the at least one additional therapy administered is reduced due to induction of at least one neoantigen and/or a T-cell response, relative to a standard dosage of Compound 1, or a pharmaceutically acceptable salt thereof, and/or the at least one additional therapy. In some embodiments, the amount of Compound 1, or a pharmaceutically acceptable salt thereof, and/or the at least one additional therapy administered is reduced due to induction of a double-stranded RNA immune response, as compared to a standard dosage of Compound 1, or a pharmaceutically acceptable salt thereof, and/or the at least one additional therapy. In some embodiments, the amount of Compound 1, or a pharmaceutically acceptable salt thereof, and/or the at least one additional therapy administered is reduced due to induction of immunogenic cell death, as compared to a standard dosage of Compound 1, or a pharmaceutically acceptable salt thereof, and/or the at least one additional therapy. In some embodiments, the administered amount of Compound 1, or a pharmaceutically acceptable salt thereof, and/or the at least one additional therapy is reduced by 10%, 15%, 20%, 25%, 30%, 35%, 40%, 45%, 50%, 75%, or 90%, relative to a standard dosage of Compound 1, or a pharmaceutically acceptable salt thereof, and/or the at least one additional therapy. In some embodiments, Compound 1, or a pharmaceutically acceptable salt thereof, and/or the at least one additional therapy is administered at least 10%, 15%, 20%, 25%, 30%, 35%, 40%, 45%, 50%, 75%, or 90% less frequently, relative to a standard dosing regimen of Compound 1, or a pharmaceutically acceptable salt thereof, and/or the at least one additional therapy. In some embodiments, the administered amount and/or dosage of Compound 1, or a pharmaceutically acceptable salt thereof, and/or the at least one additional therapy results in lower systemic toxicity and/or improved tolerance.

As used herein, the term "standard dosage" or "standard dosing regimen" refers to any usual or routine dosing regimen for a therapeutic agent, e.g., a regimen proposed by the manufacturer, approved by regulatory authorities, or otherwise tested in human subjects to meet the average patient's needs. In some embodiments, the therapeutic agent is Compound 1, or a pharmaceutically acceptable salt thereof.

Similarly, a standard dosing regimen for ipilimumab, an exemplary anti-CTLA4 checkpoint inhibitor antibody, may be 3 mg/kg administered intravenously over 90 min every 3 weeks for 4 doses (Yervoy® (ipilimumab) FDA Label Supplement, 2018). Another standard dosing regimen for ipilimumab may be 10 mg/kg administered intravenously over 90 min every 3 weeks for 4 doses, followed by 10 mg/kg every 12 weeks for up to 3 years (Yervoy® (ipilimumab) FDA Label Supplement, 2018).

As another example, a standard dosing regimen for nivolumab, an exemplary anti-PD1 checkpoint inhibitor antibody, may be 3 mg/kg administered intravenously over 60 min every 2 weeks (Opdivo® (nivolumab) FDA Label, 2015).

As another example, a standard dosing regimen for atezolizumab, an exemplary anti-PDL1 checkpoint inhibitor antibody, may be 1200 mg administered intravenously over 60 min every 3 weeks (Tecentriq® (atezolizumab) FDA Label Supplement, 2018).

In some embodiments, administration of Compound 1, or a pharmaceutically acceptable salt thereof, is initiated before administration of the at least one additional therapy. In other embodiments, administration of Compound 1, or a pharmaceutically acceptable salt thereof, is initiated after administration of the at least one additional therapy. In still other embodiments, administration of Compound 1, or a pharmaceutically acceptable salt thereof, is initiated concurrently with administration of the at least one additional therapy.

In some embodiments, administration of Compound 1, or a pharmaceutically acceptable salt thereof, is repeated at least once after initial administration. In some embodiments, Compound 1, or a pharmaceutically acceptable salt thereof, used for repeated administration is reduced relative to the amount used for initial administration. In some embodiments, the amount of Compound 1, or a pharmaceutically acceptable salt thereof, used for repeated administration is reduced relative to a standard dosage of Compound 1, or a pharmaceutically acceptable salt thereof. In some embodiments, the amount of Compound 1, or a pharmaceutically acceptable salt thereof, used for repeated administration is reduced by 10%, 15%, 20%, 25%, 30%, 35%, 40%, 45%, 50%, 75%, or 90%, relative to a standard dosage or initial dosage of Compound 1, or a pharmaceutically acceptable salt thereof.

In some embodiments, administration of the at least one additional therapy is repeated at least once after initial administration. In some embodiments, the amount of the at least one additional therapy used for repeated administration is reduced relative to the amount used for initial administration. In some embodiments, the amount of the at least one additional therapy used for repeated administration is reduced relative to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, relative to a standard dosage or initial dosage of the at least one additional therapy.

In some embodiments, repeated administration of Compound 1, or a pharmaceutically acceptable salt thereof, is concurrent with repeated administration of the at least one additional therapy. In some embodiments, administration of Compound 1, or a pharmaceutically acceptable salt thereof, is sequential or staggered with repeated administration of the at least one additional therapy.

In some embodiments, the at least one additional therapy comprises administering a checkpoint inhibitor, e.g., any checkpoint inhibitor disclosed herein. In some embodiments, the subject is intolerant, non-responsive, or poorly responsive to the checkpoint inhibitor when administered alone. In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule.

In some other embodiments, the at least one additional therapy comprises administering a neoantigen vaccine, e.g., any neoantigen vaccine disclosed herein. In some embodiments, the neoantigen vaccine comprises at least one neoantigen peptide. In some embodiments, the at least one neoantigen peptide ranges from about 10 to about 35 amino acids in length. In some embodiments, the at least one neoantigen peptide ranges from about 15 to about 25 amino acids in length. In some embodiments, the at least one neoantigen peptide comprises a known neoantigen sequence. In some embodiments, the known neoantigen sequence is a personalized neoantigen vaccine for the subject.

The term "personalized" when used to describe a neoantigen vaccine refers to a vaccine created by identifying one or more neoantigens produced in a patient, preferably as a result of an earlier exposure to Compound 1, or a pharmaceutically acceptable salt thereof, and then using one or more of those neoantigens as the basis of the vaccine for the same patient. Accordingly, in some embodiments, a patient is given Compound 1, or a pharmaceutically acceptable salt thereof, and screened for neoantigens produced by the treatment. Subsequently, in some embodiments, one or more of those neoantigens are used to create a personalized vaccine that is given to the patient. In some embodiments, Compound 1, or a pharmaceutically acceptable salt thereof, and/or peptide or mRNA vaccine may be administered to the patient once or repeatedly.

The term "universal" when used to describe a neoantigen vaccine refers to a vaccine having a peptide or mRNA sequence that is based on common or known neoantigen(s) observed by sequencing neoantigens produced in multiple patients and/or patient tissue samples, preferably as a result of an earlier exposure to Compound 1, or a pharmaceutically acceptable salt thereof. Subsequently, in some embodiments, that peptide or mRNA sequence is used for vaccinating further patients. In some embodiments, a patient is given Compound 1, or a pharmaceutically acceptable salt thereof, and then given a peptide or mRNA vaccine of known neoantigen to enhance immune response to the neoantigens produced by Compound 1, or a pharmaceutically acceptable salt thereof. In some embodiments, Compound 1, or a pharmaceutically acceptable salt thereof, and/or peptide or mRNA vaccine may be administered to the patient once or repeatedly.

In some embodiments, the known neoantigen sequence has been identified by sequencing at least one neoantigen peptide, or its encoding mRNA, induced in the subject by administering an effective amount of Compound 1, or a pharmaceutically acceptable salt thereof. In some embodiments, the at least one neoantigen peptide comprises a modified or novel neoantigen sequence induced by contacting a neoplastic cell with an effective amount of Compound 1, or a pharmaceutically acceptable salt thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier (e.g., any of the exemplary carriers described herein). In some embodiments, the at least one neoantigen peptide is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen peptide and the pharmaceutically acceptable carrier are covalently attached via a linker. In some embodiments, the neoantigen peptide and the pharmaceutically acceptable carrier are expressed as a fusion protein. In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant.

In some embodiments, the neoantigen vaccine comprises at least one neoantigen mRNA. In some embodiments, the at least one neoantigen mRNA encodes a known neoantigen sequence. In some embodiments, the known neoantigen sequence is a personalized neoantigen vaccine for the subject. In some embodiments, the known neoantigen sequence has been identified by sequencing at least one neoantigen induced in the subject by administering an effective amount of Compound 1, or a pharmaceutically acceptable salt thereof. In some embodiments, the at least one neoantigen mRNA encodes a modified or novel neoantigen sequence induced by contacting a neoplastic cell with an effective amount of Compound 1, or a pharmaceutically acceptable salt thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier (e.g., any of the exemplary carriers described herein). In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant. In some embodiments, the neoantigen mRNA is encapsulated by an encapsulating agent. In some embodiments, the encapsulating agent is a liposome. In some embodiments, the encapsulating agent is a nanoparticle.

In some embodiments, the at least one additional therapy comprises administering a cytokine or cytokine analog, e.g., any cytokine or cytokine analog disclosed herein. In some embodiments, the subject is intolerant, non-responsive, or poorly responsive to the cytokine or cytokine analog when administered alone. In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of Compound 1, or a pharmaceutically acceptable salt thereof, due to the induction and presentation of neoantigens.

In some embodiments, the at least one additional therapy comprises administering engineered tumor-targeting T-cells (i.e., CAR-T), e.g., any CAR-T therapy disclosed herein.

In some embodiments, the methods described herein may further comprise detecting one or more neoantigens and/or a T-cell response in the subject after administration of Compound 1, or a pharmaceutically acceptable salt thereof, and, optionally, continuing administration of Compound 1, or a pharmaceutically acceptable salt thereof, if one or more neoantigens and/or a T-cell response is detected. In some embodiments, detecting one or more neoantigens and/or a T-cell response in the subject indicates efficacy of treatment with Compound 1, or a pharmaceutically acceptable salt thereof. In some embodiments, treatment with the additional therapy, along with Compound 1, or a pharmaceutically acceptable salt thereof, is continued if one or more neoantigens and/or a T-cell response is detected. In some embodiments, treatment is continued at a reduced dosage and/or frequency if one or more neoantigens and/or a T-cell response is detected.

In some embodiments, the methods described herein may further comprise detecting a double-stranded RNA immune response in the subject after administration of Compound 1, or a pharmaceutically acceptable salt thereof, and, optionally, continuing administration of Compound 1, or a pharmaceutically acceptable salt thereof, if a double-stranded RNA immune response is detected. In some embodiments, detecting a double-stranded RNA immune response in the subject indicates efficacy of treatment with Compound 1, or a pharmaceutically acceptable salt thereof. In some embodiments, treatment with the additional therapy, along with Compound 1, or a pharmaceutically acceptable salt thereof, is continued if a double-stranded RNA immune response is detected. In some embodiments, treatment is continued at a reduced dosage and/or frequency if a double-stranded RNA immune response is detected.

In some embodiments, the methods described herein may further comprise detecting immunogenic cell death in the subject after administration of Compound 1, or a pharmaceutically acceptable salt thereof, and, optionally, continuing administration of Compound 1, or a pharmaceutically acceptable salt thereof, if immunogenic cell death is detected. In some embodiments, detecting immunogenic cell death in the subject indicates efficacy of treatment with Compound 1, or a pharmaceutically acceptable salt thereof. In some embodiments, treatment with the additional therapy, along with Compound 1, or a pharmaceutically acceptable salt thereof, is continued if immunogenic cell death is detected. In some embodiments, treatment is continued at a reduced dosage and/or frequency if immunogenic cell death is detected.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

In various embodiments, the present disclosure further provides a method of treating a subject having or suspected of having a neoplastic disorder, comprising: (a) administering to the subject an effective amount of Compound 1, or a pharmaceutically acceptable salt thereof, wherein administration of Compound 1, or a pharmaceutically acceptable salt thereof, induces at least one neoantigen and/or a T-cell response; (b) detecting one or more neoantigens and/or a T-cell response in the subject after administration of Compound 1, or a pharmaceutically acceptable salt thereof; and (c) continuing administration of Compound 1, or a pharmaceutically acceptable salt thereof, if one or more neoantigens and/or a T-cell response is detected. In some embodiments, detecting one or more neoantigens and/or a T-cell response in the subject indicates efficacy of treatment with Compound 1, or a pharmaceutically acceptable salt thereof. In various embodiments, Compound 1, or a pharmaceutically acceptable salt thereof, is administered on its own and/or as part of a conjugate or composition.

Combination of Compound 1 and Immune Checkpoint Inhibition:

In various embodiments, a patient having a cancer as described herein can be treated with a combination of Compound 1, or a pharmaceutically acceptable salt thereof, and a checkpoint inhibitor therapy. Immune checkpoints are inhibitory pathways that slow down or stop immune reactions and prevent excessive tissue damage from uncontrolled activity of immune cells. As used herein, the term "checkpoint inhibitor" is meant to refer to any therapeutic agent, including any small molecule chemical compound, antibody, nucleic acid molecule, or polypeptide, or any fragments thereof, that inhibits one or more of the inhibitory pathways, thereby allowing more extensive immune activity.

Treatment of patients with immune checkpoint inhibition has been shown to have robust efficacy in certain clinical indications. Recently, the FDA approved use of a checkpoint inhibitor in patients with tumors exhibiting high microsatellite instability, agnostic to the tissue lineage. This approval was based, in part, on the observation that response rates correlate positively with mutational burden (Rizvi et al. (2015) Science 348(6230):124-8; Hellmann et al. (2018) Cancer Cell 33(5):853-861). Estimates from the literature vary in absolute numbers and by lineage, but generally support that above a threshold of ~150-250 mutations, the probability of response rises. Analysis of TCGA data shows that a large percentage of adult-onset tumor lineages have comparatively low non-synonymous mutational burden (Vogelstein et al. (2013) Science 339:1549-58). Most lineages have median non-synonymous mutational rates of ~30-80 per patient, well below the thresholds for improved odds of response to checkpoint inhibitors.

For instance, HER2-positive breast cancer has been shown to have a median of ~60 non-synonymous mutations present per patient sample. However, the threshold for checkpoint inhibitor treatment efficacy, as mentioned above, is estimated to be in the range of ~150-250 non-synonymous mutations, i.e., patients above this threshold are more likely to show complete remission, partial remission, and/or stable disease, whereas patients below this threshold are more likely to exhibit progressive disease. Strategies to enhance the apparent number of non-synonymous mutations and/or neoantigens being presented on tumor cells are therefore desirable, and may enhance the overall probability of response, e.g., to checkpoint inhibitor therapies. As cytokines (and analogs thereof) act via a similar mechanism of action, such strategies may also enhance the overall probability of response to cytokine-based therapies.

Current response rates in HER2-positive breast cancer are ~15-25% (CTI NCT02129556). In various embodiments disclosed herein, treatment with Compound 1, or a pharmaceutically acceptable salt thereof, in combination with a checkpoint inhibitor and/or cytokine therapy may improve such response rates. In various embodiments, treatment with Compound 1, or a pharmaceutically acceptable salt thereof, in combination with a checkpoint inhibitor and/or cytokine therapy may apply to any adult-onset tumor, particularly those in which the median non-synonymous mutational rate is below the estimated ~150 mutations threshold. In various embodiments, exemplary cancer types suitable for treatment with Compound 1, or a pharmaceutically acceptable salt thereof, alone or in combination with an additional therapy (e.g., a checkpoint inhibitor therapy, a cytokine therapy) include but are not limited to esophageal cancer, non-Hodgkin's lymphoma, colorectal cancer, head and neck cancer, gastric cancer, endometrial cancer, pancreatic adenocarcinoma, ovarian cancer, prostate cancer, hepatocellular cancer, glioblastoma, breast cancer (e.g., HER2-positive breast cancer), lung cancer (e.g., non-small cell lung cancer), chronic lymphocytic leukemia, and acute myeloid leukemia. Other exemplary suitable cancer types are identified, e.g., in Vogelstein et al. (2013) Science 339:1549-58, which is incorporated herein by reference in its entirety.

As many checkpoint inhibitor therapies are based on chronic expression of tumor-associated antigens, regular treatment boosts are required for efficacy and for "re-boosting" reactive T-cell populations. The inducible nature of Compound 1-, or pharmaceutically acceptable salt thereof, derived neoantigens described herein provide for therapeutic dosing regimens that may be designed to enhance the immune response of neoantigen-reactive T-cells, while limiting T-cell exhaustion often caused by chronic antigen stimulation. For instance, in some embodiments, an initial dose of Compound 1, or a pharmaceutically acceptable salt thereof, is administered to a subject to trigger aberrant splicing and production of neoantigen peptides. After a period of time to allow for protein production and antigen presentation, in some embodiments, the subject is then administered an initial dose of a checkpoint inhibitor to boost and/or enhance effector T-cell priming and expansion. In some embodiments, the wait period between doses of Compound 1, or a pharmaceutically acceptable salt thereof, and checkpoint inhibitor is about 2, about 3, about 4, about 5, about 6, or about 7 days. In some embodiments, the wait period is between about 3 days and about 5 days. In some embodiments, the checkpoint inhibitor is targeted at CTLA4, OX40, CD40, and/or GITR. In some embodiments, the combination therapeutic benefit of Compound 1, or a pharmaceutically acceptable salt thereof, and a checkpoint inhibitor may be additive or superadditive.

In some embodiments, after a period to allow for T-cell priming and expansion, the subject is then administered a second or subsequent dose of Compound 1, or a pharmaceutically acceptable salt thereof, to trigger re-presentation of neoantigen peptides. In some embodiments, the wait period between an initial dose of a checkpoint inhibitor and a second or subsequent dose of Compound 1, or a pharmaceutically acceptable salt thereof, is about 2, about 3, about 4, or about 5 weeks. In some embodiments, the wait period is about 3 weeks. Following a second or subsequent dose of Compound 1, or a pharmaceutically acceptable salt thereof, in some embodiments, the immune system may engage with the neoantigen-presenting tumor cells and/or elicit tumor cell killing. In some embodiments, the subject is then administered a second or subsequent dose of the checkpoint inhibitor to further expand the memory effector T-cell population, after allowing for secondary T-cell priming and expansion.

In some embodiments, dosing of Compound 1, or a pharmaceutically acceptable salt thereof, following this exemplary initial treatment regimen can be pulsatile, i.e., Compound 1, or a pharmaceutically acceptable salt thereof, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population. At later timepoints, in some embodiments, Compound 1, or a pharmaceutically acceptable salt thereof, treatment may be combined with one or more checkpoint inhibitors targeted to restore effector functionality to exhausted T-cell populations. For example, in some embodiments, at later timepoints, Compound 1, or a pharmaceutically acceptable salt thereof, treatment may be combined with one or more checkpoint inhibitors targeted at PD1/PDL1, LAG3, and/or TIM3. In some embodiments, the pulsed nature of neoantigen presentation and priming may allow a checkpoint inhibitor and/or Compound 1, or a pharmaceutically acceptable salt thereof, to be administered less frequently and/or at lower doses. In some embodiments, the pulsed nature of neoantigen presentation may provide one or more treatment benefits for a checkpoint inhibitor (e.g., an anti-CTLA4 antibody such as ipilimumab), relative to the checkpoint inhibitor when administered without concurrent Compound 1, or a pharmaceutically acceptable salt thereof, treatment, for example, by lowering the potential risk of adverse reactions often observed with the checkpoint inhibitor's standard dosing regimen.

In certain embodiments, the checkpoint inhibitor is an inhibitor of the cytotoxic T-lymphocyte-associated antigen (CTLA4) pathway. CTLA4, also known as CD152, is a protein receptor that downregulates immune responses. CTLA4 is constitutively expressed in regulatory T-cells, but only upregulated in conventional T-cells after activation. As used herein, the term "CTLA4 inhibitor" is meant to refer to any inhibitor of CTLA4 and/or the CTLA4 pathway. Exemplary CTLA4 inhibitors include but are not limited to anti-CTLA4 antibodies. CTLA4 blocking antibodies for use in humans were developed based on the pre-clinical activity seen in mouse models of anti-tumor immunity. Exemplary anti-CTLA4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the anti-CTLA4 antibody is ipilimumab.

In certain embodiments, the checkpoint inhibitor is an inhibitor of the programmed death-1 (PD1) pathway. The programmed cell death 1 (PD1) pathway represents a major immune control switch which may be engaged by tumor cells to overcome active T-cell immune surveillance. The ligands for PD1 (PDL1 and PDL2) are constitutively expressed or can be induced in various tumors. High expression of PDL1 on tumor cells (and to a lesser extent of PDL2) has been found to correlate with poor prognosis and survival in various other solid tumor types. Furthermore, PD1 has been suggested to regulate tumor-specific T-cell expansion in patients with malignant melanoma. These observations suggest that the PD1/PDL1 pathway plays a critical role in the tumor immune evasion and may be considered an attractive target for therapeutic intervention. As used herein, the term "PD1 inhibitor" is meant to refer to any inhibitor of PD1 and/or the PD1 pathway. Exemplary PD1 inhibitors include but are not limited to anti-PD1 and anti-PDL1 antibodies. In certain embodiments, the checkpoint inhibitor is an anti-PD1 antibody. Exemplary anti-PD1 antibodies include but are not limited to nivolumab and pembrolizumab (MK-3475). Nivolumab, for example, is a fully human immunoglobulin G4 (IgG4) PD1 immune checkpoint inhibitor antibody that disrupts the interaction of the PD1 receptor with its ligands PDL1 and PDL2, thereby inhibiting the cellular immune response (Guo et al. (2017) J Cancer 8(3):410-6). In some embodiments, the anti-PD1 antibody is nivolumab. Pembrolizumab, for example, is a potent and highly-selective humanized mAb of the IgG4/kappa isotype designed to directly block the interaction between PD1 and its ligands, PDL1 and PDL2. Pembrolizumab strongly enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFNγ), and other cytokines. Exemplary anti-PDL1 antibodies include but are not limited to atezolizumab, avelumab, and durvalumab. Atezolizumab, for example, is an IgG1 humanized mAb that is reported to block the PD1/PDL1 interaction, by targeting the expressed PDL1 on numerous kinds of malignant cells. This blockage of the PD1/PDL1 pathway may stimulate the immune defense mechanisms against tumors (Abdin et al. (2018) Cancers (Basel) 10(2):32). In some embodiments, the anti-PDL1 antibody is atezolizumab.

In certain embodiments, the checkpoint inhibitor is targeted at PD1/PDL1, CTLA4, OX40, CD40, LAG3, TIM3, GITR, and/or KIR. In certain embodiments, the checkpoint inhibitor is targeted at CTLA4, OX40, CD40, and/or GITR. In certain embodiments, a checkpoint inhibitor is targeted with an inhibitory antibody or other similar inhibitory molecule (e.g., an inhibitory anti-CTLA4 or anti-PD1/PDL1 antibody). In certain other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T-cell suppression, while enhancing effector T-cell functions. Agonist anti-GITR antibodies have also been shown to make effector T-cells more resistant to the inhibition induced by regulatory T-cells (Karaki et al. (2016) Vaccines (Basel) 4(4):37). Likewise, agonist CD40 antibodies demonstrate T-cell-dependent anti-tumor activity. Activation of CD40 on dendritic cells increases cross-presentation of tumor antigens and consequently the number of activated tumor-directed effector T-cells (Ellmark et al. (2015) Oncoimmunol. 4(7): e1011484).

In certain embodiments, the checkpoint inhibitor is targeted at CTLA4 (e.g., an anti-CTLA4 antibody). In certain embodiments, targeting CTLA4 facilitates priming and activation of naïve T-cells. In certain embodiments, the checkpoint inhibitor is targeted at OX40 (e.g., an anti-OX40 antibody). In certain embodiments, targeting OX40 enhances expansion of effector T-cells. In certain embodiments, the checkpoint inhibitor is targeted at CD40 (e.g., an anti-CD40 antibody). In certain embodiments, targeting CD40 inhibits "tolerogenic" priming of T-cells and/or formation of regulatory T-cells. In certain embodiments, the checkpoint inhibitor is targeted at GITR (e.g., an anti-GITR antibody). In certain embodiments, targeting GITR inhibits activity of regulatory T-cells. In certain embodiments, the benefit of combination therapy (e.g., the effect on at least one symptom or the risk/rate of disease progression) with Compound 1, or a pharmaceutically acceptable salt thereof, and a CTLA4-, OX40-, CD40-, and/or GITR-targeted agent is additive. In some embodiments, the benefit of combination therapy with Compound 1, or a pharmaceutically acceptable salt thereof, and a CTLA4-, OX40-, CD40-, and/or GITR-targeted agent is superadditive (i.e., synergistic).

Checkpoint inhibitor treatment strategies are based on the hypothesis that treatment facilitates and/or enhances priming of T-cell responses to weakly or poorly antigenic tumors (e.g., CTLA4) or that treatment restores and/or reinvigorates T-cells that respond to tumor antigens, but have become "exhausted" due to the chronic nature of the antigen presentation (e.g., PD1, PDL1) (Chen and Mellman (2013) Immunity 39(1):1-10). Examples of suitable checkpoint inhibition therapies and agents, e.g., anti-PD1, anti-PDL1, or anti-CTLA4 antibodies, are known in the art. See, e.g., WO 2001/014424 WO 2013/173223, WO 2016/007235.

Combining these primed T-cell responses following checkpoint inhibitor therapy with treatment to induce neoantigens in tumor cells (e.g., by administration of Compound 1, or a pharmaceutically acceptable salt thereof,) to which the primed immune system can react may provide beneficial synergy. As Compound 1-, or pharmaceutically acceptable salt thereof, derived neoantigens have not yet been presented for T-cell priming, combination with a CTLA4 inhibitor may be particularly beneficial. In some embodiments, treatment comprises administering Compound 1, or a pharmaceutically acceptable salt thereof, to induce the production of neoantigens, followed before, concurrently, or thereafter by an initial administration of a CTLA4 inhibitor to stimulate CD8 T-cell priming. In some embodiments, additional administrations of an CTLA4 inhibitor are provided to the patient, e.g., to further stimulate priming and/or activation of neoantigen-reactive CD8 populations. In some embodiments, additional administrations of Compound 1, or a pharmaceutically acceptable salt thereof, can be given to the patient to increase neoantigen presentation by the tumor. Repeat administrations of Compound 1, or a pharmaceutically acceptable salt thereof, and checkpoint inhibitor therapy can occur concurrently or in staggered intervals. In some embodiments, treatment further comprises administering a PD1/PDL1 inhibitor co-treatment, e.g., to restore effector function of exhausted neoantigen-targeted T-cells within the tumor microenvironment.

The terms "combination" or "combination therapy," as used herein, refer to the administration of Compound 1, or a pharmaceutically acceptable salt thereof, together with an additional agent or therapy (e.g., a checkpoint inhibitor, a cytokine or cytokine analog, a neoantigen vaccine, CAR-T), as part of a treatment regimen intended to provide a beneficial (i.e., additive or synergistic) effect from the co-action of one or more of the administered agents. In some embodiments, the combination may also include one or more additional agents, including but not limited to chemotherapeutic agents, anti-angiogenesis agents, and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a medical condition (e.g., a neoplastic disorder). For example, in some embodiments, the two or more treatments are delivered after the subject has been diagnosed with a disease or disorder, and before the disease or disorder has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., Compound 1, or a pharmaceutically acceptable salt thereof, and a checkpoint inhibitor) are comprised in the same composition. Such compositions may be administered in any appropriate form and by any suitable route. In other embodiments, the two treatments (e.g., Compound 1, or a pharmaceutically acceptable salt thereof, and a checkpoint inhibitor) are administered in separate compositions, in any appropriate form and by any suitable route. For example, in some embodiments, a composition comprising Compound 1, or a pharmaceutically acceptable salt thereof, and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease or disorder, is greater than what would be observed with the first treatment delivered in the absence of the second treatment. In other embodiments, an analogous situation is observed with the second treatment. In some embodiments, the benefit of combination therapy (e.g., the effect on at least one symptom or the risk/rate of disease progression) is additive. In some embodiments, the benefit of combination therapy is superadditive.

In various embodiments, the present disclosure provides a method of treating a subject having or suspected of having a neoplastic disorder by administering to the subject an effective amount of Compound 1, or a pharmaceutically acceptable salt thereof; and at least one additional therapy (e.g., a checkpoint inhibitor therapy, a cytokine or cytokine analog, a neoantigen vaccine, CAR-T). In some embodiments, administration of Compound 1, or a pharmaceutically acceptable salt thereof, induces at least one neoantigen and/or a T-cell response. In some embodiments, administration of Compound 1, or a pharmaceutically acceptable salt thereof, induces a double-stranded RNA immune response. In some embodiments, administration of Compound 1, or a pharmaceutically acceptable salt thereof, induces immunogenic cell death. In some embodiments, the at least one additional therapy may comprise at least one, at least two, at least three, at least four, or at least five additional therapies. For example, in some embodiments, Compound 1, or a pharmaceutically acceptable salt thereof, may be administered in combination with two checkpoint therapies, i.e., using two different checkpoint inhibitors. In some other embodiments, Compound 1, or a pharmaceutically acceptable salt thereof, may be administered in combination with a checkpoint inhibitor therapy and a neoantigen vaccine. In some embodiments, Compound 1, or a pharmaceutically acceptable salt thereof, may be administered on its own and/or as part of a conjugate or composition.

In some embodiments of combination therapy, the administered amount of Compound 1, or a pharmaceutically acceptable salt thereof, and/or the at least one additional therapy is reduced by 10%, 15%, 20%, 25%, 30%, 35%, 40%, 45%, 50%, 75%, or 90%, relative to a standard dosage of Compound 1, or a pharmaceutically acceptable salt thereof, and/or the at least one additional therapy. In some embodiments, Compound 1, or a pharmaceutically acceptable salt thereof, and/or the at least one additional therapy is administered at least 10%, 15%, 20%, 25%, 30%, 35%, 40%, 45%, 50%, 75%, or 90% less frequently, relative to a standard dosing regimen of Compound 1, or a pharmaceutically acceptable salt thereof, and/or the at least one additional therapy. In some embodiments, the administered amount and/or dosage of Compound 1, or a pharmaceutically acceptable salt thereof, and/or the at least one additional therapy results in lower systemic toxicity and/or improved tolerance.

In some embodiments, administration of Compound 1, or a pharmaceutically acceptable salt thereof, is initiated before administration of the at least one additional therapy. In some embodiments, administration of Compound 1, or a pharmaceutically acceptable salt thereof, is initiated after administration of the at least one additional therapy. In some embodiments, administration of Compound 1, or a pharmaceutically acceptable salt thereof, is initiated concurrently with administration of the at least one additional therapy.

In some embodiments, administration of Compound 1, or a pharmaceutically acceptable salt thereof, is repeated at least once after initial administration. In some embodiments, the amount of Compound 1, or a pharmaceutically acceptable salt thereof, used for repeated administration is reduced relative to the amount used for initial administration. In some embodiments, the amount of Compound 1, or a pharmaceutically acceptable salt thereof, used for repeated administration is reduced relative to a standard dosage of Compound 1, or a pharmaceutically acceptable salt thereof. In some embodiments, the amount of Compound 1, or a pharmaceutically acceptable salt thereof, used for repeated administration is reduced by 10%, 15%, 20%, 25%, 30%, 35%, 40%, 45%, 50%, 75%, or 90%, relative to a standard dosage of Compound 1, or a pharmaceutically acceptable salt thereof.

In some embodiments, administration of the at least one additional therapy is repeated at least once after initial administration. In some embodiments, the amount of the at least one additional therapy used for repeated administration is reduced relative to the amount used for initial administration. In some embodiments, the amount of the at least one additional therapy used for repeated administration is reduced relative to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, relative to a standard dosage of the at least one additional therapy.

In some embodiments, repeated administration of Compound 1, or a pharmaceutically acceptable salt thereof, is concurrent with repeated administration of the at least one additional therapy. In some embodiments, repeated administration of Compound 1, or a pharmaceutically acceptable salt thereof, is sequential or staggered with repeated administration of the at least one additional therapy.

In various embodiments, the present disclosure provides a method of treating a subject having or suspected of having a neoplastic disorder by administering to the subject an effective amount of Compound 1, or a pharmaceutically acceptable salt thereof; and a checkpoint inhibitor therapy. In some embodiments, the checkpoint inhibitor therapy comprises administering at least one checkpoint inhibitor. In some embodiments, the subject is intolerant, non-responsive, or poorly responsive to the at least one checkpoint inhibitor when administered alone. In some embodiments, a subject may be considered non-responsive or poorly responsive to the at least one checkpoint inhibitor as determined using, e.g., the immune-related Response Criteria (irRC) and/or the immune-related Response Evaluation Criteria in Solid Tumors (irRECIST). See, e.g., Wolchok et al. (2009) Clin Cancer Res. 15(23):7412-20; Bohnsack et al. "Adaptation of the Immune-Related Response Criteria:irRECIST" (Abstract 4958) ESMO 2014. Exemplary criteria may include those used in the art to define when tumors in cancer patients improve ("respond"), remain the same ("stabilize"), or worsen ("progress") during treatment, when the treatment being evaluated is an immune-oncology drug (e.g., a checkpoint inhibitor). In some embodiments, a subject may be considered intolerant to the at least one checkpoint inhibitor if the subject presents with one or more than one adverse (grade 2+) event identified for the respective checkpoint inhibitor (e.g., ipilimumab). In some embodiments, for example, a subject may be considered intolerant to ipilimumab treatment if the subject presents with one or more adverse events selected from enterocolitis, hepatitis, dermatitis (including toxic epidermal necrolysis), neuropathy, and endocrinopathy (Yervoy® (ipilimumab) FDA Label Supplement, 2018). In some embodiments, Compound 1, or a pharmaceutically acceptable salt thereof, may be administered on its own and/or as part of a conjugate or composition.

In some embodiments, the checkpoint inhibitor is targeted at PD1/PDL1, CTLA4, OX40, CD40, LAG3, TIM3, GITR, and/or KIR. In some embodiments, the checkpoint inhibitor is targeted at CTLA4, OX40, CD40, and/or GITR. In some embodiments, the checkpoint inhibitor is targeted with an inhibitory antibody or other similar inhibitory molecule. In some other embodiments, the checkpoint inhibitor is targeted with an agonist antibody or other similar agonist molecule. In some embodiments, the checkpoint inhibitor comprises a cytotoxic T-lymphocyte-associated antigen 4 pathway (CTLA4) inhibitor. In some embodiments, the CTLA4 inhibitor is an anti-CTLA4 antibody. In some embodiments, the anti-CTLA4 antibody is ipilimumab. In some embodiments, the checkpoint inhibitor comprises a programmed death-1 pathway (PD1) inhibitor. In some embodiments, the PD1 inhibitor is an anti-PD1 antibody. In some embodiments, the anti-PD1 antibody is nivolumab. In some embodiments, the PD1 inhibitor is an anti-PDL1 antibody. In some embodiments, the anti-PDL1 antibody is atezolizumab. In some embodiments, the checkpoint inhibitor comprises a CTLA4 inhibitor and a PD1 inhibitor. In some embodiments, the checkpoint inhibitor is targeted at OX40. In some embodiments, the checkpoint inhibitor is targeted at CD40. In some embodiments, the checkpoint inhibitor is targeted at GITR. In some embodiments, the benefit of combination therapy (e.g., the effect on at least one symptom or the risk/rate of disease progression) with Compound 1, or a pharmaceutically acceptable salt thereof, and a checkpoint inhibitor (e.g., a CTLA4-, PD1/PDL1-, OX40-, CD40-, and/or GITR-targeted antibody or molecule) is additive. In some embodiments, the benefit of combination therapy with Compound 1, or a pharmaceutically acceptable salt thereof, and a checkpoint inhibitor (e.g., a CTLA4-, PD1/PDL1, OX40-, CD40-, and/or GITR-targeted antibody or molecule) is superadditive (i.e., synergistic).

In various embodiments, the present disclosure provides a method of treating a subject having or suspected of having a neoplastic disorder by administering to the subject an effective amount of Compound 1, or a pharmaceutically acceptable salt thereof; and a cytokine or cytokine analog therapy. In some embodiments, the cytokine or cytokine analog therapy comprises administering at least one cytokine or cytokine analog. In some embodiments, the subject is intolerant, non-responsive, or poorly responsive to the at least one cytokine or cytokine analog when administered alone. In some embodiments, Compound 1, or a pharmaceutically acceptable salt thereof, is administered on its own and/or as part of a conjugate or composition.

In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of Compound 1, or a pharmaceutically acceptable salt thereof, due to induction and presentation of neoantigens.

In some embodiments, the cytokine or cytokine analog comprises IL-2. In some embodiments, IL-2 boosts signals to effector cells promoting their expansion (Rosenberg (2014) J Immunol. 192(12):5451-8). In some embodiments, the cytokine or cytokine analog comprises IL-10. In some embodiments, IL-10 boosts CD8+ T-cell priming and activation (Mumm et al. (2011) Cancer Cell 20(6):781-96). In some embodiments, the cytokine or cytokine analog comprises IL-12. In some embodiments, IL-12 links the innate and adaptive immune responses to boost antigen-specific priming and targeting (Tugues et al. (2015) Cell Death Differ. 22(2):237-46). In some embodiments, the cytokine or cytokine analog comprises IL-15. In some embodiments, IL-15 boosts T-effector (CD8) cell priming and/or activation. In some embodiments, the cytokine or cytokine analog comprises IFNγ. In some embodiments, IFNγ supplements T-effector cell secretion of IFNγ. In some embodiments, the cytokine or cytokine analog comprises TNFα. In some embodiments, TNFα supplements T-effector cell secretion of TNFα.

In some embodiments, an initial dose of Compound 1, or a pharmaceutically acceptable salt thereof, is administered to a subject to trigger aberrant splicing and production of neoantigen peptides. After a period to allow for protein production and antigen presentation, in some embodiments, the subject is then administered an initial dose of a cytokine or cytokine analog to boost and/or enhance effector T-cell priming and expansion. In some embodiments, the wait period between doses of Compound 1, or a pharmaceutically acceptable salt thereof, and cytokine or cytokine analog is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of Compound 1, or a pharmaceutically acceptable salt thereof, and a cytokine or cytokine analog may be additive or superadditive.

In some embodiments, after a period to allow for T-cell priming and expansion, the subject is then administered a second or subsequent dose of Compound 1, or a pharmaceutically acceptable salt thereof, to trigger re-presentation of neoantigen peptides. In some embodiments, the wait period between an initial dose of a cytokine or cytokine analog and a second or subsequent dose of Compound 1, or a pharmaceutically acceptable salt thereof, is about 2, about 3, about 4, or about 5 weeks. In some embodiments, the wait period is about 3 weeks. In some embodiments, subsequent doses of the cytokine or cytokine analog may be administered, e.g., interspersed between subsequent doses of Compound 1, or a pharmaceutically acceptable salt thereof. Following a second or subsequent dose Compound 1, or a pharmaceutically acceptable salt thereof, in some embodiments, the immune system may engage with the neoantigen-presenting tumor cells and/or elicit tumor cell killing. In some embodiments, dosing of Compound 1, or a pharmaceutically acceptable salt thereof, following this exemplary initial treatment regimen can be pulsatile, i.e., Compound 1, or a pharmaceutically acceptable salt thereof, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

Combination of Compound 1 and Neoantigen Vaccine:

In various embodiments, a patient having a cancer as described herein can be treated with a combination of Compound 1, or a pharmaceutically acceptable salt thereof, and a neoantigen vaccine. In various embodiments, Compound 1, or a pharmaceutically acceptable salt thereof, is administered on its own and/or as part of a conjugate or composition.

As used herein, the term "neoantigen vaccine" refers to a pooled sample of neoantigen peptides or mRNAs, for example at least two, at least three, at least four, at least five, or more neoantigen peptides. The term "vaccine" refers to a composition for generating immunity for the prophylaxis and/or treatment of a disease (e.g., a neoplastic disorder, e.g., a hematological malignancy or solid tumor). Accordingly, vaccines are medicaments which comprise immunogenic agents and are intended to be used in humans or animals for generating specific defense and protective substance by vaccination. A neoantigen vaccine can additionally include a pharmaceutically acceptable carrier, diluent, excipient, and/or adjuvant.

As used herein, the term "immunogenic" refers to any agent or composition that can elicit an immune response, e.g., a T-cell response. The immune response can be antibody- or cell-mediated, or both.

In some embodiments, a patient is given Compound 1, or a pharmaceutically acceptable salt thereof, and then given a peptide or mRNA vaccine of known neoantigen to enhance immune response to the neoantigens produced by Compound 1, or a pharmaceutically acceptable salt thereof. In some other embodiments, a patient is given Compound 1, or a pharmaceutically acceptable salt thereof, and screened for neoantigens produced by the treatment. Subsequently, one or more of those neoantigens are used to create a personalized vaccine that is given to the patient. In either of these embodiments, Compound 1, or a pharmaceutically acceptable salt thereof, and/or peptide or mRNA vaccine may be administered to the patient once or repeatedly.

In various embodiments, a suitable neoantigen for a vaccine can be identified by screening a panel of transcripts with altered splicing and robust expression from one or more tissue samples in a patient (e.g., from a tumor biopsy). In some embodiments, variant protein sequences are identified in the screened sample based on translation across the aberrantly spliced mRNA junction while retaining portions of the protein sequence (up to 12 amino acids) flanking the junction-spanning amino acid changes. In some embodiments, these junction-spanning peptide fragments are scanned for high affinity binding to MHC1 alleles, e.g., using a tool such as NetMHC1 (Nielsen et al. (2003) Protein Sci 12(5):1007-17; Andretta and Neilsen (2016) Bioinformatics 32(4):511-7). These results allow for filtering of the neopeptides to those that are predicted high affinity binders for a unique patient HLA allele makeup as well as assembly of pools of neopeptides predicted to be broadly binding to HLA alleles that are present with high frequencies in different populations (Maiers et al. (2007) Hum Immunol 68(9):779-88). In various embodiments, the identified neopeptides are then formulated as a vaccine, e.g., by conjugation to a suitable carrier or adjuvant (Ott et al. (2017) Nature 547(7662):217-21), or for delivery as an mRNA (Sahin et al. (2017) Nature 547(7662):222-6).

In some embodiments, the selected neoantigen is based on a screen of an individual patent's tumor response to Compound 1, or a pharmaceutically acceptable salt thereof. In other embodiments, a neoantigen is chosen, e.g., based on screening a panel of samples from different patients to identify common neoantigens produced by Compound 1, or a pharmaceutically acceptable salt thereof, and then used as a universal vaccine for future patients. Without being bound by theory, this latter option would avoid the need to sequence and analyze the unique mutation status of each patient's tumor because the chosen neoantigens are not dependent on tumor mutation but rather mimic a neoantigen produced by Compound 1, or a pharmaceutically acceptable salt thereof, and recognized by the body as foreign. This may allow for the formulation of a bulk vaccine that would be broadly immunogenic across a large percentage of patients, expediting the initiation of a treatment regime. Patients would be vaccinated according to the schedules outlined above and, following completion of the vaccination, could be further treated with Compound 1, or a pharmaceutically acceptable salt thereof, to induce expression of the neoantigen peptides. In some embodiments, patients may be administered Compound 1, or a pharmaceutically acceptable salt thereof, before, at the same time as, or after vaccination. Compound 1, or a pharmaceutically acceptable salt thereof, and/or vaccine may be administered once or more than once.

In various embodiments, a vaccine may comprise one or more than one neoantigen peptide or mRNA. In various embodiments, a vaccine may comprise one or more than one long neoantigen peptide. Such "long" neoantigen peptides, in various embodiments, undergo efficient internalization, processing, and cross-presentation in professional antigen-presenting cells such as dendritic cells, and have been shown to induce cytotoxic T-cells in humans (Melief and van der Burg (2008) Nat Rev Cancer 8(5):351-60). In various embodiments, a neoantigen peptide is extended to comprise the neoantigen peptide sequence itself in addition to flanking amino acid sequences. In various embodiments, the extended peptide sequence facilitates the uptake of protein by antigen-presenting cells, e.g., dendritic cells. In various embodiments, the extended peptide sequence enables efficient antigen presentation and T-cell priming in models with different HLA isotypes.

In some embodiments, a neoantigen vaccine comprises at least one neoantigen peptide. In some embodiments, a neoantigen vaccine comprises at least 2, at least 3, at least 4, at least 5, at least 6, at least 7, at least 8, at least 9, at least 10, at least 12, at least 15, or at least 20 neoantigen peptides. In some embodiments, the neoantigen peptide(s) range from about 5 to about 50 amino acids in length. In some embodiments, the neoantigen peptide(s) range from about 10 to about 35 amino acids in length. In some embodiments, the neoantigen peptide(s) range from about 15 to about 25 amino acids in length.

In various embodiments, the present disclosure provides a method of treating a subject having or suspected of having a neoplastic disorder by administering to the subject an effective amount of Compound 1, or a pharmaceutically acceptable salt thereof; and a neoantigen vaccine. In various embodiments, Compound 1, or a pharmaceutically acceptable salt thereof, is administered on its own and/or as part of a conjugate or composition. A neoantigen vaccine may be, e.g., a peptide or mRNA neoantigen vaccine. Also provided herein, in various embodiments, are neoantigen vaccines comprising at least one neoantigen peptide or at least one neoantigen mRNA. In some embodiments, a neoantigen vaccine comprises at least one neoantigen peptide. In some other embodiments, a neoantigen vaccine comprises at least one neoantigen mRNA.

In some embodiments, the neoantigen vaccine comprises at least one neoantigen peptide. In some embodiments, the at least one neoantigen peptide ranges from about 10 to about 35 amino acids in length. In some embodiments, the at least one neoantigen peptide ranges from about 15 to about 25 amino acids in length.

In some embodiments, the at least one neoantigen peptide comprises a known neoantigen sequence. In some embodiments, the known neoantigen sequence is a personalized neoantigen vaccine for the subject. In some embodiments, the known neoantigen sequence has been identified by sequencing at least one neoantigen induced in the subject by administering an effective amount of Compound 1, or a pharmaceutically acceptable salt thereof. In some embodiments, the at least one neoantigen peptide comprises a modified or novel neoantigen sequence induced by contacting a neoplastic cell with an effective amount of Compound 1, or a pharmaceutically acceptable salt thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier. In various embodiments, a neoantigen peptide or mRNA can be linked to a suitable carrier to help elicit an immune response. Exemplary carriers for linking to immunogenic agents (e.g., a neoantigen peptide or mRNA) include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. Other carriers for stimulating or enhancing an immune response include cytokines such as IL-1, IL-1α and β peptides, IL-2, γINF, IL-10, GM-CSF, and chemokines, such as M1P1α and β and RANTES. Immunogenic agents can also be linked to peptides that enhance transport across tissues, as described, e.g., in WO 97/17613 and WO 97/17614. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen peptide may be linked to the pharmaceutically acceptable carrier. Immunogenic agents can be linked to carriers by chemical cross-linking. Techniques for linking an immunogenic peptide to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described in Jansen et al. ((1982) Immun Rev. 62:185). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt. In some embodiments, the neoantigen peptide and the pharmaceutically acceptable carrier are covalently attached via a linker.

Neoantigen and other such immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein. In some embodiments, the neoantigen peptide and the pharmaceutically acceptable carrier are expressed as a fusion protein.

In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant (e.g., an adjuvant as described herein).

In some embodiments, the neoantigen vaccine comprises at least one neoantigen mRNA. In some embodiments, the at least one neoantigen mRNA encodes a known neoantigen sequence. In some embodiments, the known neoantigen sequence is a personalized neoantigen vaccine for the subject. In some embodiments, the known neoantigen sequence has been identified by sequencing at least one neoantigen induced in the subject by administering an effective amount of Compound 1, or a pharmaceutically acceptable salt thereof. In some embodiments, the at least one neoantigen mRNA encodes a modified or novel neoantigen sequence induced by contacting a neoplastic cell with an effective amount of Compound 1, or a pharmaceutically acceptable salt thereof. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier. In some embodiments, the at least one neoantigen mRNA is linked to the pharmaceutically acceptable carrier. In some embodiments, the pharmaceutically acceptable carrier is selected from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant (e.g., an adjuvant as described herein).

In some embodiments, the neoantigen mRNA is encapsulated by an encapsulating agent. In some embodiments, the encapsulating agent protects the neoantigen mRNA from degradation and improves vaccine delivery (McNamara et al. (2015) J Immunol Res. 2015:794528). In some embodiments, the encapsulating agent is a liposome. In some embodiments, the liposome is a cationic liposome such as N-[1-(2,3-dioleoloxy)propyl]-N,N,N-trimethyl ammonium chloride 1 (DOTAP). In some embodiments, the encapsulating agent is a nanoparticle. In some embodiments, the nanoparticle protects the neoantigen mRNA from nuclease degradation and/or enhances cell uptake and/or delivery efficiency. In some embodiments, the nanoparticle may be engineered to be fully degradable. In some embodiments, the nanoparticle is a biodegradable core-shell structured nanoparticle with a pH responsive poly-(b-amino ester) (PBAE) core enveloped by a phospholipid shell (Su et al. (2011) Mol Pharm. 8(3):774-87). In some embodiments, such nanoparticles are particularly efficient in delivering mRNA in vivo and eliciting an anti-tumor immune response.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is selected from a B-cell malignancy, a leukemia, a lymphoma, and a myeloma. In some embodiments, the hematological malignancy is selected from acute myeloid leukemia and multiple myeloma. In some embodiments, the solid tumor is selected from breast cancer, gastric cancer, prostate cancer, ovarian cancer, lung cancer, uterine cancer, salivary duct carcinoma, melanoma, colon cancer, and esophageal cancer. In some embodiments, the solid tumor is selected from HER2-positive breast cancer, gastric adenocarcinoma, and prostate cancer.

As used herein, "adjuvant" refers to a substance that is capable of increasing, amplifying, or modulating an immune response to an accompanying immunogenic agent, e.g., a neoantigen peptide or mRNA. In certain embodiments, a neoantigen of the present disclosure can be administered in combination with adjuvants, i.e., substances that do not themselves cause adaptive immune responses, but amplify or modulate the response to an accompanying neoantigen. A variety of adjuvants can be used in combination with the disclosed neoantigens, in order to elicit an immune response. Preferred adjuvant(s) augment the intrinsic response to the neoantigen without causing conformational changes in the neoantigen that would affect the qualitative form of the response.

In certain embodiments, the adjuvant is an aluminum salt (alum), such as aluminum hydroxide, aluminum phosphate, and aluminum sulphate. Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP)), or other bacterial cell wall components. Other adjuvants are oil-in-water emulsions and include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfuidizer (Microfluidics), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem) containing 2% squalene, 0.2% Tween 80, and one or more bacterial cell wall components from the group consisting of monophosphoryllipid A (MPL), trehalose dimycolate (TDM), and cell wall skeleton (CWS), for example MPL-FCWS (Detox™). In some embodiments, the adjuvant is a saponin, such as Stimulon™ (QS21) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

An adjuvant can be administered with an immunogenic agent (e.g., a neoantigen peptide or mRNA) as a single composition, or can be administered before, concurrent with, or after administration of the immunogenic agent. In some embodiments, the immunogenic agent and adjuvant can be packaged and supplied in the same vial or can be packaged in separate vials and mixed before use. In some embodiments, the immunogenic agent and adjuvant can be packaged with a label, indicating the intended therapeutic application. In some embodiments, if the immunogenic agent and adjuvant are packaged separately, the packaging can include instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al. (1998) Adv Drug Deliv Rev. 32:173-186) alone or optionally in combination with any of alum, QS21, and MPL and all combinations thereof are suitable for human administration.

EXAMPLES

Example 1: Synthesis of Compound 1

In addition to the exemplary synthesis of Compound 1 set forth below, synthesis of Compound 1 is described in U.S. Pat. No. 9,481,669 B2 and International Application No. PCT/US2016/062525, all of which are incorporated by reference.

Microwave heating was done using a Biotage Emrys Liberator or Initiator microwave. Column chromatography was carried out using an Isco Rf200d. Solvent removal was carried out using either a Büchi rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

The following abbreviations are used herein:
MeOH: Methanol
DMF: Dimethylformamide
KHMDS: Potassium bis(trimethylsilyl)amide
LCMS: Liquid chromatography-mass spectrometry
TBS CI: tert-Butyldimethylsilyl chloride
THF: Tetrahydrofuran
TLC: Thin-layer chromatography Materials: The following compounds are commercially available and/or can be prepared in a number of ways well known to one skilled in the art of organic synthesis. Compounds of Formula I can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions are apparent to one skilled in the art, and alternate methods are therefore indicated. The starting materials for the examples are either commercially available or are readily prepared by standard methods from known materials.

LCMS Information
Mobile phases: A (0.1% formic acid in $H_2O$) and B (0.1% formic acid in acetonitrile).
Gradient: B 5%→95% in 1.8 minutes.
Column: Acquity BEH C18 column (1.7 um, 2.1×50 mm).

U.S. Pat. Nos. 7,884,128 and 7,816,401, both entitled: Process for Total Synthesis of Pladienolide B and Pladienolide D, describe methods known in the art for synthesis of Pladienolide B and D. Synthesis of Pladienolide B and D may also be performed using methods known in the art and described in Kanada et al., "Total Synthesis of the Potent Antitumor 20 Macrolides Pladienolide B and D," *Angew. Chem. Int. Ed.* 46:4350-4355 (2007). Kanada et al. and PCT application publication WO 2003/099813, entitled: Novel Physiologically Active Substances, describe methods known in the art for the synthesis of E7107 (Compound 45 of WO '813) from Pladienolide D (11107D of WO '813). A corresponding U.S. patent is U.S. Pat. No. 7,550,503 to Kotake et al.

Synthesis of (S)-2-(1-((1-phenyl-1H-tetrazol-5-yl)sulfonyl)propan-2-yl)pyridine

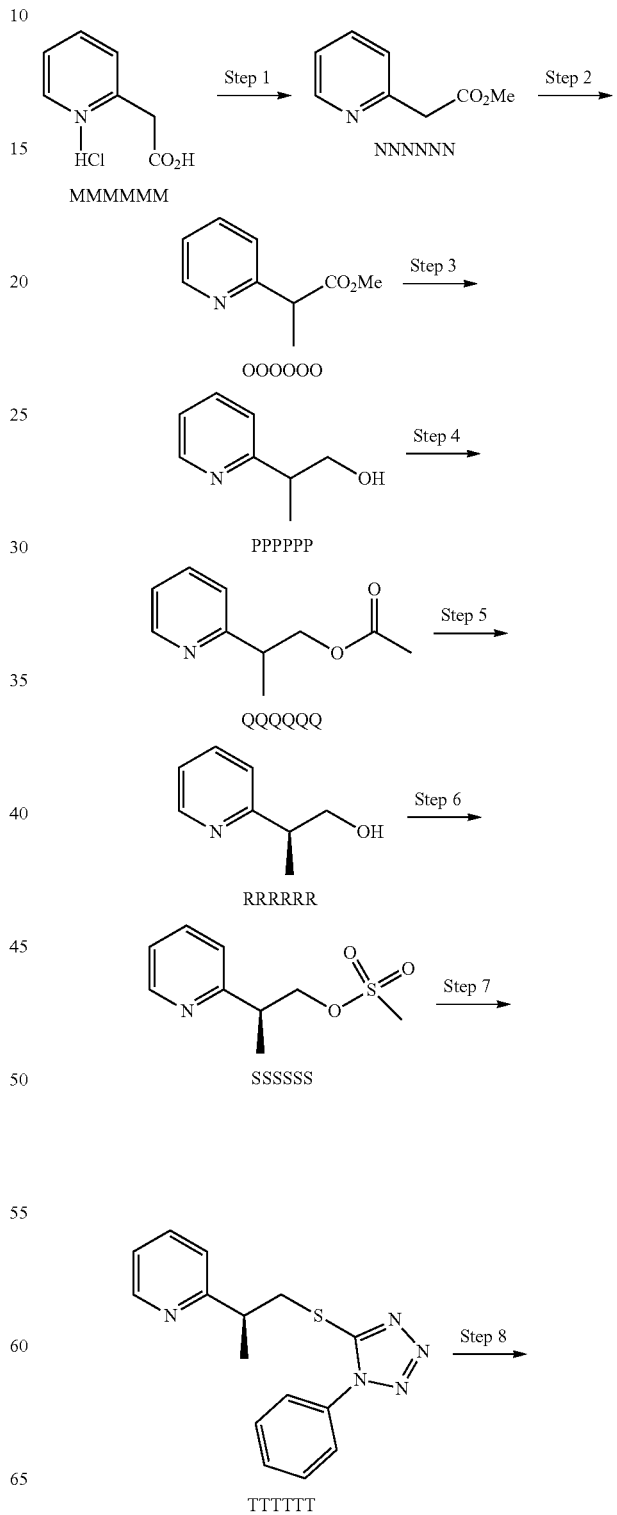

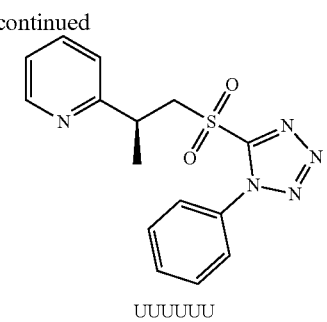

UUUUUU

Step 1: To a solution of 2-(pyridin-2-yl)acetic acid hydrochloride salt MMMMMM (50.0 g, 288.0 mmol, 1.0 equiv.) in methanol (500 mL, 0.5M) at 0° C. was added thionyl chloride (31.5 mL, 432.0 mmol, 1.5 equiv.) dropwise. The reaction was stirred at 0° C. for 60 minutes or until the reaction was determined to be complete by LCMS or TLC. The reaction was carefully quenched with sodium carbonate and the aqueous layer extracted with ethyl acetate. The combined organic layers were washed with water, brine, dried over magnesium sulfate, filtered, and concentrated in vacuo. The resulting product (NNNNNN, 41.5 g, 275.0 mmol, 95%) was used in the next step without further purification.

Step 2: To a solution of ester NNNNNN (41.5 g, 275.0 mmol, 1.0 equiv.) in THF (1500 mL, 0.2 M) at 0° C. was added sodium 2-methylpropan-2-olate (28.6 g, 288.3 mmol, 1.05 equiv.) and the reaction mixture was stirred for 30 minutes at 0° C. before addition of iodomethane (34.3 mL, 549.1 mmol, 2.0 equiv.). The reaction was stirred at room temperature for 1 hour or until the reaction was determined to be complete by LCMS or TLC. The reaction was quenched with ammonium chloride and the excess of solvent was removed in vacuo. The crude material was then extracted with ethyl acetate. The combined organic layers were washed with brine, and dried over magnesium sulfate. After filtration, the mixture was concentrated in vacuo. The resulting methyl ester (OOOOOO, 41.3 g, 250 mmol, 91%) was advanced without purification.

Step 3: To a solution of methyl ester OOOOOO (43.0 g, 260.3 mmol, 1.0 equiv.) in THF (1500 mL, 0.1M) at 0° C. was added lithium aluminum hydride (312 mL, 312.4 mmol, 1.2 equiv., solution in THF) dropwise. The reaction was allowed to warm gradually to 0° C. for 30 minutes and then to room temperature for 1 hour or until the reaction was determined to be complete by LCMS or TLC. The reaction was carefully quenched with water, sodium hydroxide and water. After stirring the mixture for 30 minutes, the white precipitate was filtered off and the solvent was removed in vacuo. The reaction was then extracted with diethyl ether and the combined organic fractions were washed with water, brine, dried over magnesium sulfate, filtered, and concentrated in vacuo. The resulting alcohol (PPPPPP, 30.0 g, 219.0 mmol, 84%) was advanced without purification.

Step 4: To a solution of alcohol PPPPPP (30.0 g, 219.0 mmol, 1.0 equiv.) in dichloromethane (700 mL, 0.3 M) at 0° C. was added triethylamine (61.5 mL, 437.4 mmol, 2.0 equiv.), and DMAP (2.7 g, 21.9 mmol, 0.1 equiv.). Acetic anhydride (24.8 mL, 262.4 mmol, 1.2 equiv.) was added and the reaction mixture was stirred for 30 minutes or until the reaction was determined to be complete by LCMS or TLC. The reaction was quenched with ammonium chloride, the organic layer was washed with brine, dried over magnesium sulfate and filtered. The resulting solution was then evaporated and the crude acetate (QQQQQQ, 37.0 g, 206.0 mmol, 94%) was used in the following step without further purification.

Step 5: A solution of acetate QQQQQQ (39.4 g, 219.8 mmol, 1.0 equiv.) was dissolved in diethyl ether (100 mL) and then 118 g of silica gel was added. The excess of ether was removed in vacuo and the crude solid was then diluted in pH 7 aqueous buffer (1970 mL, 0.1 M) (sodium hydroxide/sodium phosphate monobasic/water). Porcine pancreatic lipase type II (3.3 g, (15 mg/mmol)) was added and the reaction was stirred at 37° C. for four hours or until determined to be complete by TLC or LCMS. (After four hours, conversion reached 40% according to ELSD and the enantiomeric excess was determined by chiral SFC, and showed an enantiomeric ratio of 13:1 S:R). (SFC condition: SFC Investigator (Waters/Thar), software: Chromscope v1.2, method: Isocratic 15% co-solvent 95:5 Heptane:IPA+ 0.1% DEA over 10 minutes, Column: Lux-Amylose-2, 4.6×250 mm, 5 µm, Total Flow: 4 ml/min (3.80 mL from $CO_2$ pump, 0.20 mL from modifier pump), Oven temp set to 35° C. and system pressure set to 100 bar, Retention Times: desired and major (S)-enantiomer 6.9 min, minor (R)-enantiomer 8.4 min). The silica gel was filtered off and the aqueous layer was extracted with ethyl acetate three times. The combined organic layers were washed with brine, dried over magnesium sulfate and concentrated. The product was purified by silica gel column chromatography (hexanes: ethyl acetate as eluant) to afford the desired alcohol (RRRRRR, 12.5 g, 91 mmol, 41%).

Step 6: To a solution of alcohol RRRRRR (12.5 g, 91.0 mmol, 1.00 equiv.) in dichloromethane (570 mL, 0.16 M) at room temperature was added triethylamine (13.9 mL, 100.1 mmol, 1.1 equiv). The reaction was cooled down to 0° C. and then methanesulfonyl chloride (7.44 mL, 95.5 mmol, 1.05 equiv) was added. The reaction was stirred at 0° C. for 30 minutes or until determined to be complete by TLC or LCMS. The reaction was quenched with sodium bicarbonate and the layers were separated. The aqueous layer was then extracted with dichloromethane. The combined organic layers were washed with brine, dried over magnesium sulfate, and concentrated in vacuo. The resulting sulfonate SSSSSS (19.2 g, 89 mmol, 98%) was advanced without additional purification.

Step 7: To a solution of sulfonate SSSSSS (19.2 g, 89 mmol, 1.0 equiv.) in DMF (120 mL, 0.1M) at room temperature was added cesium carbonate (40.7 g, 125.0 mmol, 1.4 equiv.) and l-phenyl-1H-tetrazole-5-thiol (19.1 g, 107.1 mmol, 1.2 equiv.). The resulting mixture was stirred at 50° C. for 48 hours, or until determined to be complete by TLC or LCMS. After cooling the mixture to room temperature, brine was added and the aqueous layer was extracted three times with diethyl ether. The combined organic layers were washed with water, brine, and dried over magnesium sulfate. After filtration, the solvent was removed in vacuo and the residue was purified using silica gel column chromatography (hexanes/ethyl acetate) to give the desired product (TTTTTT, 28.9 g, 88 mmol, 99%).

Step 8: To a solution of sulfide TTTTTT (31.5 g, 105.9 mmol, 1.0 equiv.) in EtOH (700 mL, 0.1 M) at –10° C. was added ammonium molybdate tetrahydrate (6.5 g, 5.3 mmol, 0.05 equiv.) and hydrogen peroxide (108 mL, 1060 mmol, 5.0 equiv., 33% aqueous solution). The reaction was stirred at –10° C. for four hours or until determined to be complete by TLC or LCMS. The reaction was quenched with water and sodium metabisulfite solution. The crude product was collected by filtration and was purified by silica gel column chromatography (hexanes:ethyl acetate as eluant) to afford the desired product (UUUUUU, 23.2 g, 70.4 mmol, 66%). ¹H NMR (400 MHz, CHLOROFORM-d) δ: 1.50 (d, J=7.03 Hz, 3H) 1.66 (br. s., 1H) 3.75 (m, 1H) 3.94 (dd, J=14.81, 5.02 Hz, 1H) 4.55 (dd, J=14.68, 7.91 Hz, 1H) 7.14-7.22 (m, 2H) 7.29 (s, 1H) 7.57-7.70 (m, 6H) 8.44-8.49 (m, 1H).

The colorless oil was then recrystallized using toluene/heptane (1/1) (1 mL of toluene and 1 mL of heptane per 100 mg of compound. Heat gently the mixture to mix the two solvents. Let the mixture cool down to room temperature for 12 h. (If no recrystallization is observed, add one crystal to the solution. The crystal will help to get crystals via seeding process.) The crystals formed slowly over time. They could be isolated via filtration or removing liquid layer via pipette. The crystals were then washed with heptane and then quickly with toluene. The er of the sulfone was analyzed before and after recrystallization. (SFC conditions: SFC condition: SFC Investigator (Waters/Thar), software: Chromscope v1.2, method: Isocratic 10% co-solvent MeOH over 10 minutes, Column: ChiralPak IC, 4.6×250 mm, 5 μm, Total Flow: 4 ml/min (3.80 ml from CO₂ pump, 0.20 ml from modifier pump), Oven temp set to 35° C. and system pressure set to 100 bar, Retention Times: desired and major (S)-enantiomer 3.5 min, minor (R)-enantiomer 3.8 min).

Exemplary Synthesis of Compound 1

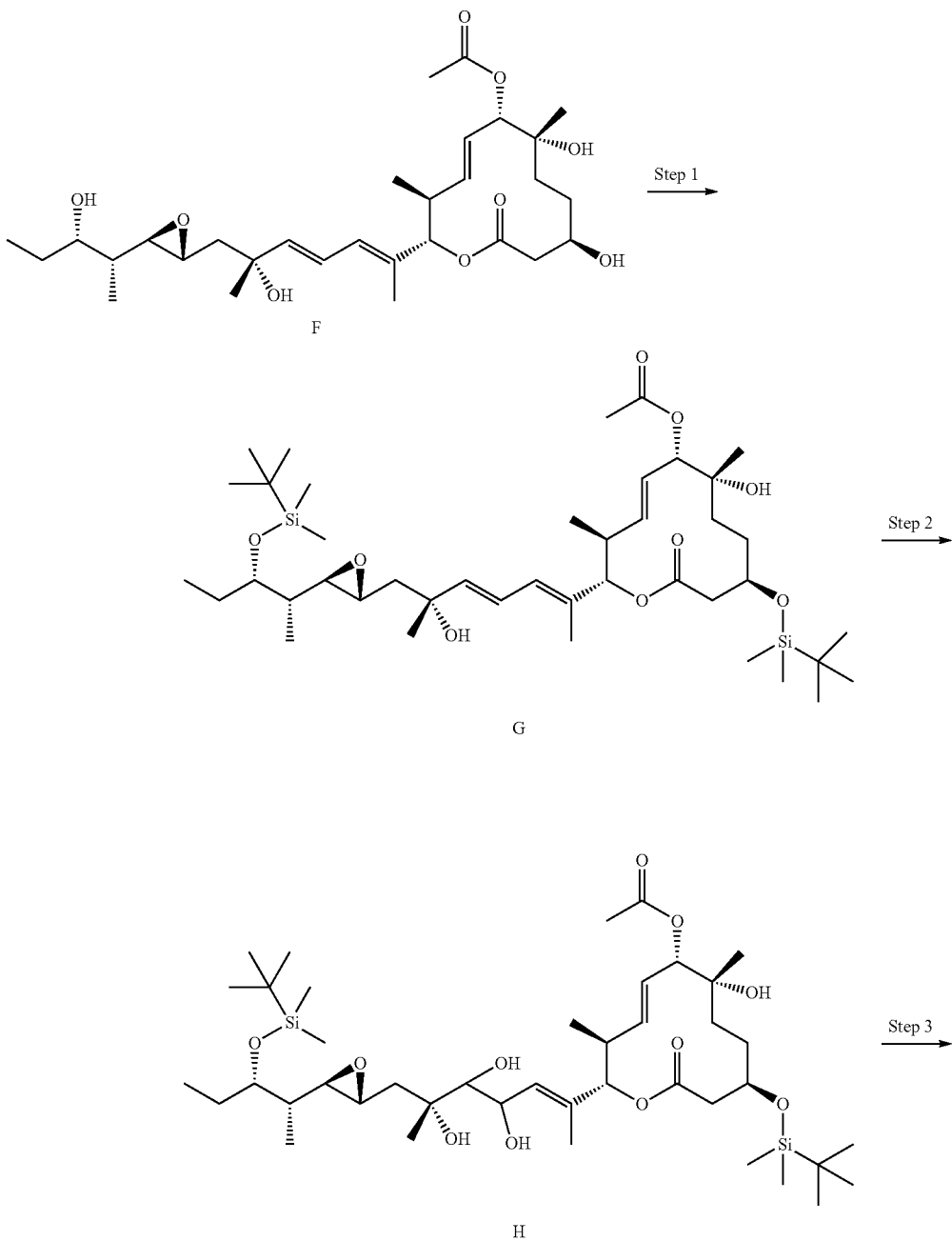

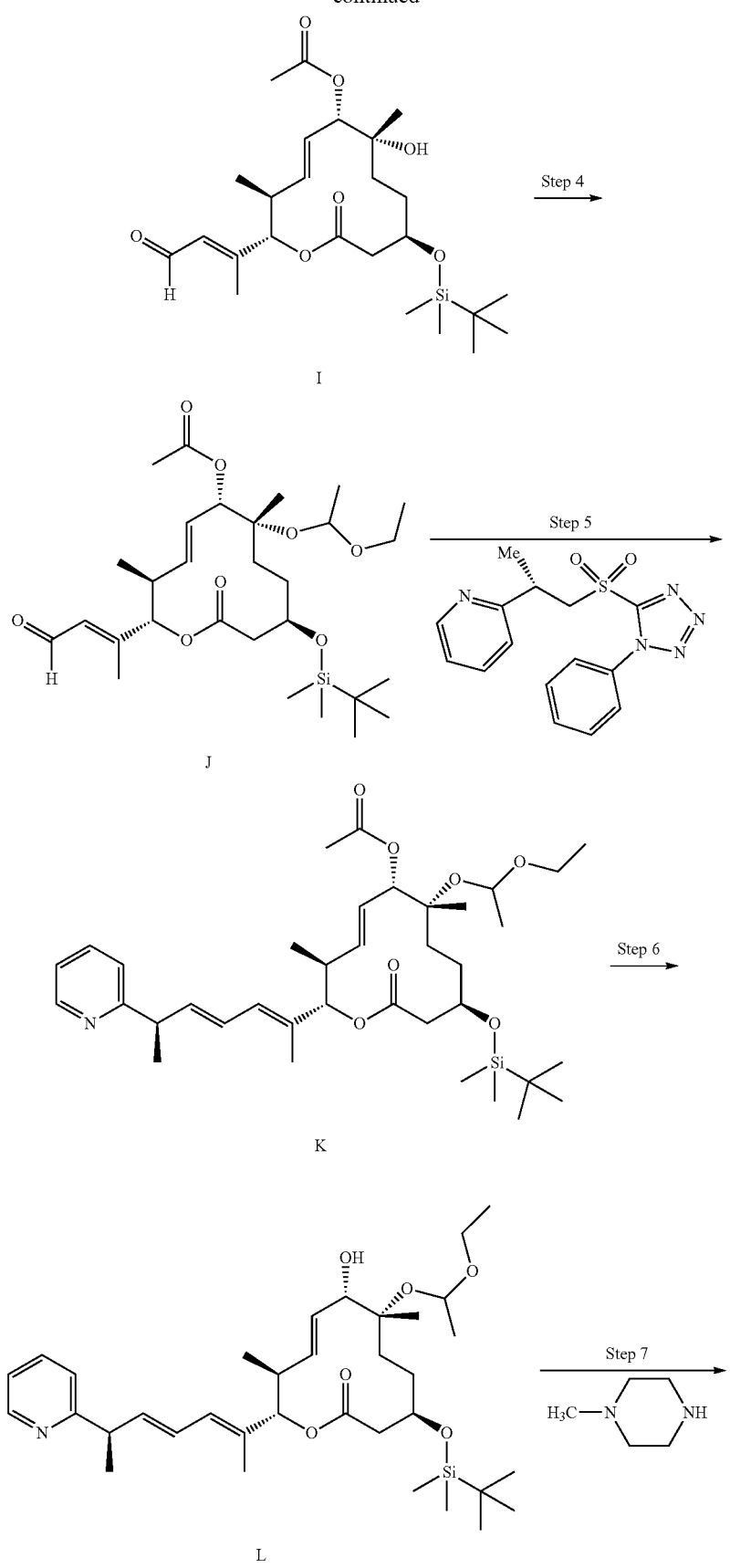

-continued

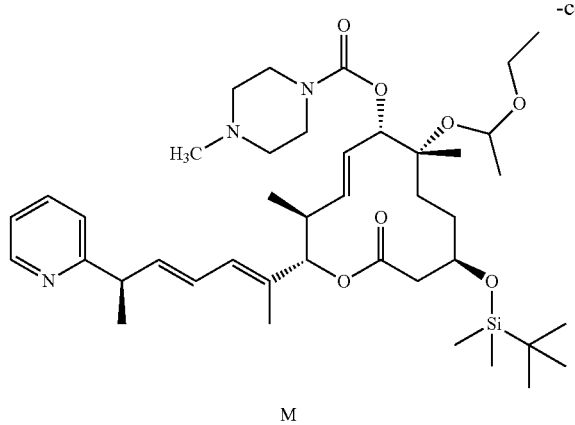

M

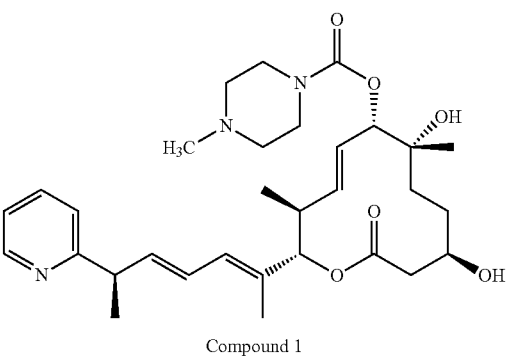

Compound 1

Step 1: Synthesis of (2S,3S,6S,7R,10R,E)-10-((tert-butyldimethylsilyl)oxy)-2-((R,2E,4E)-7-((2R,3R)-3-((2S,3S)-3-((tert-butyldimethylsilyl)oxy)pentan-2-yl)oxiran-2-yl)-6-hydroxy-6-methylhepta-2,4-dien-2-yl)-7-hydroxy-3,7-dimethyl-12-oxooxacyclododec-4-en-6-yl acetate. A solution of pladienolide D (F, 5.3 g, 9.7 mmol, 1.0 equiv.) under nitrogen in DMF (80 mL, 0.1M) at 0° C. was treated with imidazole (4.6 g, 67.8 mmol, 7.0 equiv.) and TBSCI (7.3 g, 48.4 mmol, 5.0 equiv.). The reaction was allowed to warm to room temperature and stirred for 20 hours, or until the reaction was determined to be complete by LCMS or TLC. The reaction was extracted with ethyl acetate and the organic layer was washed with brine, dried over sodium sulfate, filtered, and concentrated in vacuo. The resulting oil was purified by silica gel column chromatography (hexanes/ethyl acetate as eluant) to afford the desired product (G, 7.5 g, 9.6 mmol, 99%).

Step 2: Synthesis of (2S,3S,6S,7R,10R,E)-10-((tert-butyldimethylsilyl)oxy)-2-((6R,E)-7-((2R,3S)-3-((ted-butyldimethylsilyl)oxy)pentan-2-yl)oxiran-2-yl)-4,5,6-trihydrox-6-methylhept-2-en-2-yl)-7-hydroxy-3,7-dimethyl-12-oxooxacyclododec-4-en-6-yl acetate. To a solution of olefin G (7.6 g, 9.7 mmol, 1.0 equiv.) in degassed TEF:H₂O (210 mL:21 mL, 0.01M) under nitrogen at 0° C. was added osmium tetroxide (24.4 mL, 1.9 mmol, 0.2 equiv., 2.5% solution in tert-butanol) followed by N-methylmorpholine N-oxide (2.3 g, 19.5 mmol, 2.0 equiv.). The reaction was allowed to warm to room temperature and stirred for 13 hours, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (H, 6.8 g, 8.3 mmol, 86%).

Step 3: Synthesis of (2S,3S,6S,7R,10R,E)-10-((tert-butyldimethylsilyl)oxy)-7-hydroxy-3,7-dimethyl-12-oxo-2-((E)-4-oxobut-2-en-2-yl)oxacyclododec-4-en-6-yl acetate. To a solution of diol H (7.9 g, 9.7 mmol, 1.0 equiv.) in benzene (350 mL, 0.03M) under nitrogen at room temperature was added lead tetraacetate (8.6 g, 19.4 mmol, 2.0 equiv.). The reaction was stirred for 30 minutes, or until the reaction was determined to be complete by LCMS or TLC. The reaction was concentrated and purified by silica gel column chromatography (hexane/ethyl acetate as eluent) to afford the desired product (I, 2.5 g, 5.26 mmol, 54%).

Step 4: Synthesis of (2S,3S,6S,7R,10R,E)-10-((tert-butyldimethylsilyl)oxy)-7-(1-ethoxyethoxy)-3,7-dimethyl-12-oxo-2-((E)-4-oxobut-2-en-2-yl)oxacyclododec-4-en-6-yl acetate. To a solution of aldehyde I (1.4 g, 2.9 mmol, 1.0 equiv.) in THF (9.5 mL, 0.5M) was added ethoxyethene (11.1 mL, 40.0 equiv.) and pyridinium p-toluenesulfonate (0.07 g, 0.3 mmol, 0.1 equiv.) at room temperature. The reaction was stirred for 24 hours, or until the reaction was determined to be complete by LCMS or TLC. The reaction was quenched with sodium bicarbonate and diluted with ethyl acetate. The ethyl acetate was washed with water, brine, dried over magnesium sulfate, filtered, and concentrated in vacuo. The resulting oil was purified by silica gel column chromatography (hexane/ethyl acetate as eluent) to afford the desired product (J, 1.2 g, 2.2 mmol, 75%).

Step 5: Synthesis of (2S,3S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl) acetate. To a solution of (S)-2-(I-((I-phenyl-1H-tetrazol-5-yl)sulfonyl)propan-2-yl)pyridine (UUUUU) (695.0 mg, 2.1 mmol, 1.5 equiv.) in THF (20 mL, 0.06M) under nitrogen at −78° C. was added KHMDS (4.2 mL, 2.1 mmol, 1.5 equiv.) dropwise and the reaction was stirred for 20 minutes. Then aldehyde J (780.0 mg, 1.4 mmol, 1.0 equiv.) in THF (1.0 mL) was added dropwise. The reaction was stirred at −78° C. for 90 minutes and then allowed to warm to −20° C. for 1 hour. The reaction was quenched with ammonium chloride, diluted with ethyl acetate, and warmed to room temperature. The organic layer was washed with water, brine, dried over magnesium sulfate, filtered, and concentrated in vacuo. The resulting oil was purified by silica gel column chromatography (hexane/ethyl acetate as eluent) to afford the desired Julia product (K, 490 mg, 0.7 mmol, 53%).

Step 6: Synthesis of (4R,7R,8S,11S,E)-4-((tert-butyldimethylsilyl)oxy)-7-(I-ethoxyethoxy)-8-hydroxy-7,11-di methyl-12-((R,2E,4E)-6-(pyridin-2-yl)hepta-2,4-dien-2-yl)oxacyclododec-9-en-2-one. To a solution of acetate K (490 mg, 0.7 mmol, 1.0 equiv.) in methanol (15 mL, 0.05M) at room temperature was added potassium carbonate (155 mg, 0.4 mmol, 1.5 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting foamy solid (L, 459 mg, 0.7 mmol, 100%) was advanced into the next step without additional purification.

Step 7: Synthesis of (2S,3S,6S,7R,10R,E)-10-((tert-butyldimethylsilyl)oxy)-7-(1-ethoxyethoxy)-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate. To a solution of alcohol L (459 mg, 0.7 mmol, 1.0 equiv.) in dichloromethane (0.5 mL, 0.1 M) at room temperature was added N,N-dimethylaminopyridine (27.3 mg, 0.2 mmol, 0.3 equiv.) and triethylamine (1.0 mL, 7.4 mmol, 10.0 equiv.) followed by 4-nitrophenyl chloroformate (451 mg, 02.2 mmol, 3:0 equiv.). The reaction was stirred at room temperature for three hours. Next, N-methyl-piperazine (299 mg, 2.98 mmol, 4.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluant) to afford the desired product (M, 553 mg, 0.75 mmol, 100%).

Step 8: Synthesis of (2S,3S,6S,7R,10R,E)-7,10-dihydroxy-3,7-dimethyl-12-oxo-2-((R,2E,4E)-6-(pyridin-2-yl)hepta-2,4-dien-2-yl)oxacyclododec-4-en-6-yl 4-methylpiperazine-1-carboxylate (Compound 1). To a solution of silyl ether (M, 553 mg, 0.74 mmol, 1.0 equiv.) in methanol (20 mL, 0.04M) at room temperature was added p-methoxytoluenesulfonic acid (425 mg, 2.2 mmol, 3.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired Compound 1 (184 mg, 0.33 mmol, 44%). $^1$H NMR (400 MHz, CHLOROFORM-d) δ: 0.82-1.00 (m, 3H) 1.22-1.48 (m, 8H) 1.50-1.63 (m, 1H) 1.66-1.83 (m, 4H) 1.97 (s, 1H) 2.07 (s, 1H) 2.33 (s, 3H) 2.40 (br. s., 3H) 2.45-2.68 (m, 3H) 3.44-3.61 (m, 5H) 3.74 (dd, J=14.2, 7.2 Hz, 2H) 5.04 (d, J=9.3 Hz, 1H) 5.17 (d, J=10.5 Hz, 1H) 5.57-5.76 (m, 2H) 6.02 (dd, J=15.1, 7.5 Hz, 1H) 6.13 (d, J=10.8 Hz, 1H) 6.34 (ddd, J=15.1, 10.7, 1.0 Hz, 1H) 7.14 (t, J=6.2 Hz, 1H) 7.18 (d, J=7.4 Hz, 1H) 7.63 (t, J=7.3 Hz, 1H) 8.57 (d, J=5.1 Hz, 1H). MS (ES+)=556.4 [M+H].

Example 2: Administration of Compound 1 in Combination with A Checkpoint Inhibitor Efficacy Study Protocol: Mouse Colon Cancer Syngeneic Model CT26 colon cancer cells (0.25×10$^6$; ATCC Cat # CRL-2638) were implanted subcutaneously into the right flank of eight-week old female Balb/c mice (Envigo) in 100 μL of PBS lacking matrigel. CT26 tumors were allowed to grow to an average of ~100 mm$^3$ before animals were enrolled onto the efficacy study. Each treatment group contained 12 mice. Mice were treated with Compound 1, an anti-CTLA4 antibody (Bio X Cell Catalog Number: BE0164 (αCTLA4 9D9)), or a combination at doses and routes of administration as shown in FIG. 1. Compound 1 was formulated in a composition containing 5% ethanol and 95% methylcellulose solution (0.5% methylcellulose. The anti-CTLA4 antibody was formulated in phosphate buffer solution at pH 7.0. Tumors were measured 3 times per week for up to 19 days. Tumor volumes were calculated using the ellipsoid formula:

Tumor Volume=(length×width$^2$)/2

Efficacy Study Results

Figure 1B:
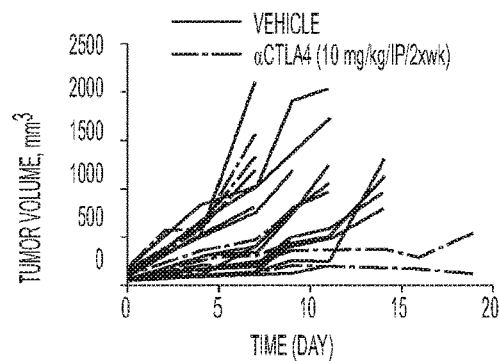
Figure 1C:
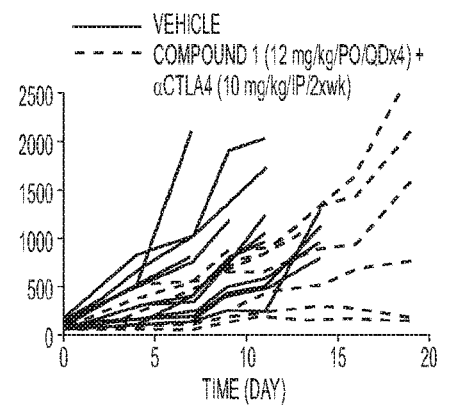
Figure 1C:
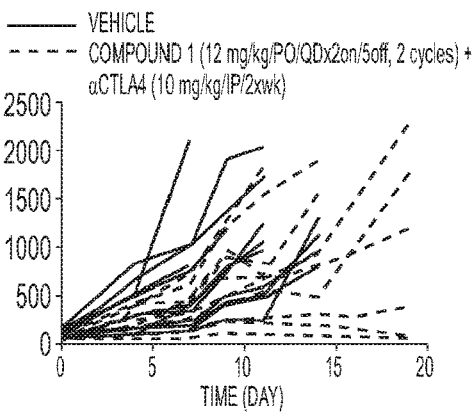
Figure 1C:
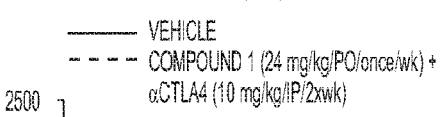
Figure 1C:
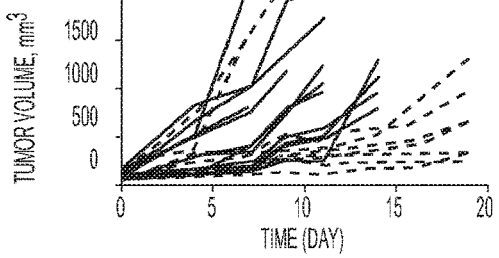

Treatment of animals harboring CT26 syngeneic tumors with Compound 1 at any dose level or schedule did not result in noticeable antitumor activity when growth curves were compared to those of vehicle treated controls (FIG. 1A). Treatment with an antibody targeting the immune-checkpoint CTLA4 ("anti-CTLA4") at 10 mg/kg twice per week resulted in substantial tumor growth delay in only 2 out of 12 animals (FIG. 1B). However, it was surprisingly found that after administration of Compound 1 in combination with anti-CTLA4, a significant increase in the response rate was observed (FIG. 1C).

The invention claimed is:

1. A method of treating a subject having or suspected of having a neoplastic disorder, comprising administering to the subject a therapeutically effective amount of Compound 1

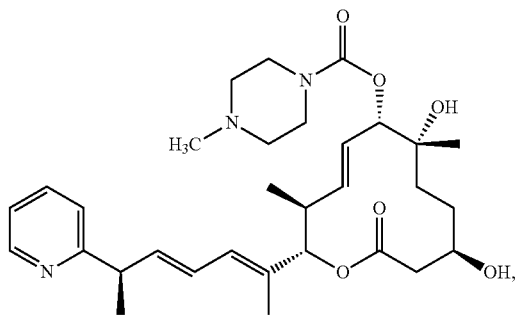 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C]

or a pharmaceutically acceptable salt thereof, and at least one additional therapy comprising a CTLA4 inhibitor, and wherein the neoplastic disorder is selected from myelodysplastic syndrome, chronic lymphocytic leukemia, acute lymphoblastic leukemia, chronic myelomonocytic leukemia, acute myeloid leukemia, and colon cancer.

2. The method of claim 1, wherein administration of the Compound 1, or a pharmaceutically acceptable salt thereof, is initiated before, after, or concurrently with administration of the at least one additional therapy.

3. The method of claim 1, wherein administration of the Compound 1, or a pharmaceutically acceptable salt thereof, and/or the at least one additional therapy is repeated at least once after initial administration.

4. The method of claim 1, wherein the CTLA4 inhibitor is an anti-CTLA4 antibody.

5. The method of claim 1, wherein the at least one additional therapy comprises at least one, at least two, at least three, at least four, or at least five additional therapies.

6. The method of claim 1, further comprising detecting one or more neoantigens and/or a T-cell response in the subject after administration of the Compound 1, or a pharmaceutically acceptable salt thereof.

7. The method of claim 6, further comprising continuing administration of the Compound 1, or a pharmaceutically acceptable salt thereof, after one or more neoantigens and/or a T-cell response is detected.

8. The method of claim 6, further comprising administering a neoantigen vaccine, wherein the neoantigen vaccine comprises one or more neoantigens detected in the subject after administration of the Compound 1, or a pharmaceutically acceptable salt thereof.

9. The method of claim 1, wherein the subject has a non-synonymous mutational burden of about 150 mutations or less.

10. The method of claim 1, wherein the neoplastic disorder is myelodysplastic syndrome.

11. The method of claim 1, wherein the Compound 1, or a pharmaceutically acceptable salt thereof, is administered as part of a conjugate.

12. The method of claim 4, wherein the anti-CTLA4 antibody is ipilimumab.

* * * * *